(12) United States Patent
Hu et al.

(10) Patent No.: US 7,078,589 B2
(45) Date of Patent: Jul. 18, 2006

(54) ISOLATED NEMATODE REGULATED GENE PROMOTER AND USE THEREOF

(75) Inventors: Xu Hu, Johnston, IA (US); Guihua Lu, Johnston, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 98 days.

(21) Appl. No.: 10/837,104

(22) Filed: Apr. 30, 2004

(65) Prior Publication Data

US 2004/0248304 A1  Dec. 9, 2004

Related U.S. Application Data

(60) Provisional application No. 60/467,623, filed on May 2, 2003.

(51) Int. Cl.
  *C12N 15/09* (2006.01)
  *C12N 15/82* (2006.01)
  *A01H 5/00* (2006.01)
(52) U.S. Cl. .................. 800/287; 800/278; 800/298; 800/312; 435/320.1; 435/468; 435/69.1; 536/24.1
(58) Field of Classification Search ................ 800/287, 800/278, 298, 295, 312, 279; 435/468, 430, 435/320.1, 69.1; 536/24.1
See application file for complete search history.

(56) References Cited

U.S. PATENT DOCUMENTS

| | | | |
|---|---|---|---|
| 5,750,386 | A | 5/1998 | Conkling et al. |
| 5,994,627 | A | 11/1999 | Lagudah |
| 6,006,470 | A | 12/1999 | Geoghegan et al. |
| 6,228,992 | B1 | 5/2001 | Jessen et al. |
| 6,252,138 | B1 | 6/2001 | Karimi et al. |
| 6,448,471 | B1 | 9/2002 | Puzio et al. |
| 2003/0177536 | A1 | 9/2003 | Grundler et al. |

FOREIGN PATENT DOCUMENTS

| | | |
|---|---|---|
| WO | WO 92/21757 | 12/1992 |
| WO | WO 99/26483 | 6/1999 |

OTHER PUBLICATIONS

Kim et al. Plant Molecular Biology, vol. 24, pp. 105-117, (1994).*
Keller et al. The Plant Cell, vol. 3, pp. 1051-1061, (1991).*
Urwin, et al., Continual Green-Fluorescent Protein Monitoring of Cauliflower Mosaic Virus 35S Promoter Activity in Nematode-Induced Feeding Cells in *Arabidopsis thaliana*, MPMI, (1997), 10(3): 394-400.
Puzio, et al., Isolation of regulatory DNA regions related to differentiation of nematode feeding structures in *Arabidopsis thaliana*, Physiol and Mol Plant Pathol, (1998), 53: 177-193.
Puzio, et al., Isolation of a gene from *Arabidopsis thaliana* related to nematode feeding structures, NCBI, (1999), Accession Y11994.
Puzio, et al., Isolation of a gene from *Arabidopsis thaliana* related to nematode feeding structures GENE, (1999), 239: 163-172.
Puzio, et al., Isolation of regulatory DNA regions related to differentiation of nematode feeding structures in *Arabidopsis thaliana*, (2000), NCBI, Accession AJ249204.
Puzio, et al., Promoter analysis of pyk20, a gene from *Arabidopsis thaliana*, Plant Sci, (2000), 157:245-255.
Puzio, et al., Plasmodiophora brassicae-induced expression of pyk20, an *Arabidopsis thaliana* gene with glutamine-rich domain, Physiol and Mol Plant Pathol, (2000), 56: 79-84.

* cited by examiner

*Primary Examiner*—Medina A. Ibrahim
(74) *Attorney, Agent, or Firm*—Pioneer Hi-Bred International, Inc.

(57) ABSTRACT

The present invention relates to nematode-regulated promoter and polypeptide-encoding nucleotide sequences and their use in creating or enhancing nematode-resistance in plants. Nucleic acid molecules comprising a nematode-resistance sequence operably linked to a nematode-regulated promoter and vectors, plant cells, plants, and transformed seeds containing such constructs are provided. Methods for the use of such constructs in repressing or inducing expression of a nematode-resistance sequence in a plant are also provided. In addition, methods are provided for conferring or improving nematode resistance in plants by repression or induction of nematode-resistance sequences.

21 Claims, 2 Drawing Sheets

Figure 1: Sequence alignment of Arabidopsis and soybean pyk20:

```
Soy-pyk    MKRGNEEEKSAGPMFPRLHVNDAEKGGPRAPPRNKMALYEQFSIPSQRFNPHLPR--KPN
pyk20      MKRGKDEEKILEPMFPRLHVNDADKGGPRAPPRNKMALYEQLSIPSQRFGDHGTMNSRSN
           ****:.***    *********:***************:*******. *   :.*

Soy-pyk    SSSNIVPPPTSSTEGNGRERSYISRQSDDGARSNTSLVQLERRKKVDDGIHVYTCSRIDQ
pyk20      NTSTLVHPGPSSQP-CGVERNLSVQHLDSSAANQATEKFVSQMSFMEN---VRSSAQHDQ
           .:*..:* * .**     * **.   :: *..* .:::   :.: . :::   * :.:: **

Soy-pyk    SNDKMLESFNGKKLTPFGARNFCYSVAVQNGGDKDTTQFGFLPADMRKDARKGNEANPHV
pyk20      -RKMVREEEDFAVPVYINSRRSQSHGRTKSGIEKEKHTPMVAPSSHHSIR--FQEVNQTG
           .. : *. :   . :.:*.        ..:* :*:.   .*:. :.    :*.*

Soy-pyk    SSSRQKLKLSVKP------KSSGEIIDSLVMQAKVIPNQEDQDYSVPNINRLHQDDACLQ
pyk20      SKQNVCLATCSKPEVRDQVKANARSGGFVISLDVSVTEEIDLEKSASSHDRVNDYNASLR
           *... *  . **      *:...  . ::     :.:: * : *...:*::: :*.*:

Soy-pyk    KECVAGSQSNDIEHGGDLLNSTRDMDNGNALVPRGCFHSAANQTHPLEATNDAEYHDTRT
pyk20      QE----SRNRLYRDGG--KTRLKDTDNGAESHLATENHSQEGHGSPEDIDNDREYSKSRA
           :*    *:..  ..**    . :* ***     **  .: * :  ** **  ..:*:

Soy-pyk    GGPIQKGNFDESDNISKISTVTNLSSLIVSPDDVVGILGQKHFWKARRKIANQQSVFAVQ
pyk20      CASLQQINEEASDDVSDDSMVDSISSIDVSPDDVVGILGQKRFWRARKAIANQQRVFAVQ
           ..:*: *  : **::*. * *  .:**: *************:**:**: ***** *****

Soy-pyk    VFELHRLIKVQQLIAASPDVLLEDGAFMGKFPLMGSPPKNKNISLEVVVEPQ-QQNPKQK
pyk20      LFELHRLIKVQKLIAASPDLLLDEISFLGKVSAKSYPVKKLLPSEFLVKPPLPHVVVKQR
           :********** :******:**::  :*:**..  . * *:   *  :*   * :   **:

Soy-pyk    NDSE-KLNHKTECSAENAVAKKKSFSSPKNGSHH--TNHTPFSGTPHQANEASDNKTSPW
pyk20      GDSEKTDQHKMESSAENVVG-RLS-----NQGHHQQSNYMPFANNPPASPAPNGYCFPPQ
           .***  .:** *.****.*. : *      * .** :*: **:...*  :  ... .*

Soy-pyk    CFNQAPGHQWLIPVMSPSEGLVYKPYPGPGFMGTMNGGCGGPFGQAPLGATFMNPAYQFP
pyk20      PPPSGNHQQWLIPVMSPSEGLIYKPHPGMAHTGHYGGYYG---------HYMPTPMVMP
            ..  :**************:***:**  .  * * *        :* .. :*

Soy-pyk    ASHPVVGVSPFVPPASHAYFPSFG-MPVVNQATSGSTVEQVNQFAAQGSHGQNGHSYIEG
pyk20      QYHPGMG---F-PPPGNGYFPPYGMMPTIMNPYCSSQQQQQQQPNEQ--MNQFGH---PG
           ** :*    * **...:.***.:* **.: :. ..*  :*    :*   .* **    *

Soy-pyk    TDFNTHHNQS-SSNLPVLKNGATLHVKKSQASKERGLQGSTISSPSEMAQGIRAGK----
pyk20      NLQNTQQQQQRSDNEPAPQQQQQPTKSYPRARKSR--QGSTGSSPS-GPQGISGSKSFRP
           .  **:::*. *.* *. ::        . ..:* *.*  **** ****  .*** ..*

Soy-pyk    ---IAEG---NDAHSLSLQAVETRQQT--------------QVIKVVPHNRKSATESAARI
pyk20      FAAVDEDSNINNAPEQTMTTTTTTTRTTVTQTTRDGGGVTRVIKVVPHNAKLASENAARI
           : *..  *:* . :: :. *  :*             :******** * *:*.****

Soy-pyk    FQSIQEERKQHDLV--
pyk20      FQSIQEERKRYDSSKP
           *********:.:*
```

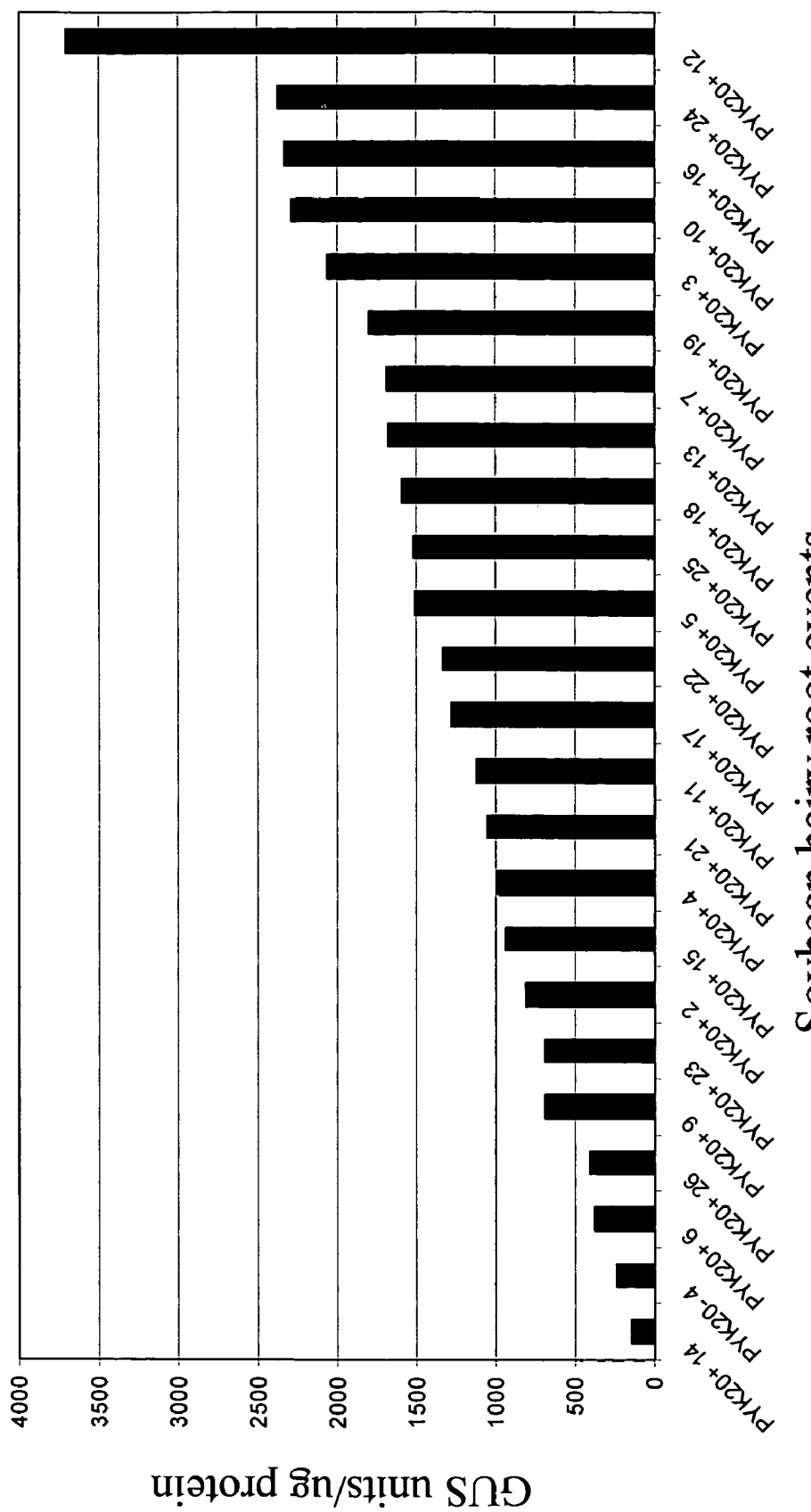
Figure 2  GUS screening of *SoyPyk20* positive events

SEQUENCE LISTING

<160> NUMBER OF SEQ ID NOS: 11

<210> SEQ ID NO 1
<211> LENGTH: 2094
<212> TYPE: DNA
<213> ORGANISM: Glycine max
<220> FEATURE:
<221> NAME/KEY: CDS
<222> LOCATION: (1)...(2094)
<223> OTHER INFORMATION: Coding region of pyk20 homologue clone

<400> SEQUENCE: 1

```
atg aag aga ggg aac gag gaa gag aag tcg gcg ggg cca atg ttc cca      48
Met Lys Arg Gly Asn Glu Glu Glu Lys Ser Ala Gly Pro Met Phe Pro
 1               5                  10                  15 agg ctg cat gta aat gat gca gag aaa gga ggg cca aga gca ccg cca      96
Arg Leu His Val Asn Asp Ala Glu Lys Gly Gly Pro Arg Ala Pro Pro
             20                  25                  30 agg aac aag atg gcc ctc tat gaa cag ttc agt att cca tct cag agg     144
Arg Asn Lys Met Ala Leu Tyr Glu Gln Phe Ser Ile Pro Ser Gln Arg
         35                  40                  45 ttc aat cca cac ctg cca cga aaa cca aat tct tct tct aac ata gtt     192
Phe Asn Pro His Leu Pro Arg Lys Pro Asn Ser Ser Ser Asn Ile Val
     50                  55                  60 cct cca cca act tcc tca act gag gga aat ggc cgt gag aga agt tat     240
Pro Pro Pro Thr Ser Ser Thr Glu Gly Asn Gly Arg Glu Arg Ser Tyr
 65                  70                  75                  80 att tct cgc caa tct gat gat gga gca agg tca aac act tca ttg gtg     288
Ile Ser Arg Gln Ser Asp Asp Gly Ala Arg Ser Asn Thr Ser Leu Val
                 85                  90                  95 caa ctt gaa cgg aga aaa aaa gta gat gat ggc att cat gtg tac act     336
Gln Leu Glu Arg Arg Lys Lys Val Asp Asp Gly Ile His Val Tyr Thr
            100                 105                 110 tgc tcg agg att gat caa tcc aat gat aaa atg ctg gag agt ttt aat     384
Cys Ser Arg Ile Asp Gln Ser Asn Asp Lys Met Leu Glu Ser Phe Asn
        115                 120                 125 ggg aaa aaa ttg act cct ttt ggt gct agg aat ttt tgt tat tca gtt     432
Gly Lys Lys Leu Thr Pro Phe Gly Ala Arg Asn Phe Cys Tyr Ser Val
    130                 135                 140 gct gtg caa aat ggt ggt gac aag gat aca aca caa ttt ggc ttc ctt     480
Ala Val Gln Asn Gly Gly Asp Lys Asp Thr Thr Gln Phe Gly Phe Leu
145                 150                 155                 160 cct gct gat atg aga aaa gat gcg agg aag ggg aat gag gca aat cca     528
Pro Ala Asp Met Arg Lys Asp Ala Arg Lys Gly Asn Glu Ala Asn Pro
                165                 170                 175 cat gta agc tca agt aga cag aaa cta aaa ttg tct gtc aaa ccc aaa     576
His Val Ser Ser Ser Arg Gln Lys Leu Lys Leu Ser Val Lys Pro Lys
            180                 185                 190 tca agt gga gaa att att gac agt cta gtg atg caa gcc aag gtg att     624
Ser Ser Gly Glu Ile Ile Asp Ser Leu Val Met Gln Ala Lys Val Ile
        195                 200                 205 cca aat caa gag gat caa gat tat tct gtg cca aat ata aac agg tta     672
Pro Asn Gln Glu Asp Gln Asp Tyr Ser Val Pro Asn Ile Asn Arg Leu
    210                 215                 220 cat cag gat gat gct tgc cta cag aag gag tgt gtg gct ggg tcc caa     720
His Gln Asp Asp Ala Cys Leu Gln Lys Glu Cys Val Ala Gly Ser Gln
225                 230                 235                 240 tcc aat gac atc gag cat ggt ggt gat ctc ctt aac tct aca agg gat     768
Ser Asn Asp Ile Glu His Gly Gly Asp Leu Leu Asn Ser Thr Arg Asp
                245                 250                 255
```

```
                                                                 -continued atg gat aat gga aat gcg ctc gta cca aga ggc tgt ttt cat tct gca    816
Met Asp Asn Gly Asn Ala Leu Val Pro Arg Gly Cys Phe His Ser Ala
    260                 265                 270 gcg aac caa act cac cca ctt gag gct acc aat gat gct gaa tat cac    864
Ala Asn Gln Thr His Pro Leu Glu Ala Thr Asn Asp Ala Glu Tyr His
275                 280                 285 gat act cgg act gga ggc ccg ata cag aag ggg aat ttt gat gaa agt    912
Asp Thr Arg Thr Gly Gly Pro Ile Gln Lys Gly Asn Phe Asp Glu Ser
        290                 295                 300 gac aac att tcc aag atc tcc act gta aca aat tta tca agt ctg ata    960
Asp Asn Ile Ser Lys Ile Ser Thr Val Thr Asn Leu Ser Ser Leu Ile
305                 310                 315                 320 gtt tct cct gat gat gtt gta ggg ata tta ggt caa aaa cat ttc tgg   1008
Val Ser Pro Asp Asp Val Val Gly Ile Leu Gly Gln Lys His Phe Trp
                325                 330                 335 aaa gca aga aga aaa att gcc aat caa cag agt gtg ttt gca gtc caa   1056
Lys Ala Arg Arg Lys Ile Ala Asn Gln Gln Ser Val Phe Ala Val Gln
            340                 345                 350 gtg ttt gaa ttg cac aga ctg att aag gtc caa cag cta att gct gca   1104
Val Phe Glu Leu His Arg Leu Ile Lys Val Gln Gln Leu Ile Ala Ala
        355                 360                 365 tca ccg gat gtt ttg ctt gaa gat ggt gct ttc atg gga aaa ttt cct   1152
Ser Pro Asp Val Leu Leu Glu Asp Gly Ala Phe Met Gly Lys Phe Pro
370                 375                 380 ttg atg ggt tct cct cct aaa aat aaa aat atc tca ttg gaa gtg gtt   1200
Leu Met Gly Ser Pro Pro Lys Asn Lys Asn Ile Ser Leu Glu Val Val
385                 390                 395                 400 gta gag cct cag caa caa aat cct aag cag aaa aac gat tct gaa aag   1248
Val Glu Pro Gln Gln Gln Asn Pro Lys Gln Lys Asn Asp Ser Glu Lys
                405                 410                 415 cta aac cat aaa aca gaa tgt tca gct gag aat gca gtt gcg aaa aaa   1296
Leu Asn His Lys Thr Glu Cys Ser Ala Glu Asn Ala Val Ala Lys Lys
            420                 425                 430 aaa tct ttt tcg tcc ccg aaa aat ggt agc cac cat aca aat cac acc   1344
Lys Ser Phe Ser Ser Pro Lys Asn Gly Ser His His Thr Asn His Thr
        435                 440                 445 cca ttt tca gga act cca cac cag gca aat gaa gct tct gat aat aaa   1392
Pro Phe Ser Gly Thr Pro His Gln Ala Asn Glu Ala Ser Asp Asn Lys
450                 455                 460 aca agt ccc tgg tgt ttc aat cag gca cct gga cat caa tgg tta att   1440
Thr Ser Pro Trp Cys Phe Asn Gln Ala Pro Gly His Gln Trp Leu Ile
465                 470                 475                 480 cct gtc atg tct cct tct gaa ggg ctt gtc tac aag cca tat cct ggg   1488
Pro Val Met Ser Pro Ser Glu Gly Leu Val Tyr Lys Pro Tyr Pro Gly
                485                 490                 495 cct gga ttt atg gga aca atg aat gga gga tgc ggc ggg cca ttc ggg   1536
Pro Gly Phe Met Gly Thr Met Asn Gly Gly Cys Gly Gly Pro Phe Gly
            500                 505                 510 caa gca cct ctc ggt gct act ttc atg aat cct gcc tat caa ttc cca   1584
Gln Ala Pro Leu Gly Ala Thr Phe Met Asn Pro Ala Tyr Gln Phe Pro
        515                 520                 525 gct tct cat cca gta gtt ggg gtt tca ccg ttt gtc cct cca gcc agt   1632
Ala Ser His Pro Val Val Gly Val Ser Pro Phe Val Pro Pro Ala Ser
530                 535                 540 cat gcc tac ttc cct tcc ttt ggc atg cca gta gtg aat caa gca aca   1680
His Ala Tyr Phe Pro Ser Phe Gly Met Pro Val Val Asn Gln Ala Thr
545                 550                 555                 560 tca gga tca act gtt gaa cag gtg aac cag ttt gct gca caa ggt tct   1728
Ser Gly Ser Thr Val Glu Gln Val Asn Gln Phe Ala Ala Gln Gly Ser
```

```
                        565                 570                 575
cat ggt caa aat ggt cat tca tat ata gag gga acc gat ttt aac act         1776
His Gly Gln Asn Gly His Ser Tyr Ile Glu Gly Thr Asp Phe Asn Thr
            580                 585                 590 cat cat aac caa agc tca tct aac ctg cca gtt ctg aag aat gga gct         1824
His His Asn Gln Ser Ser Ser Asn Leu Pro Val Leu Lys Asn Gly Ala
        595                 600                 605 acg cta cat gtt aaa aaa tct cag gcg tct aag gag aga ggg tta caa         1872
Thr Leu His Val Lys Lys Ser Gln Ala Ser Lys Glu Arg Gly Leu Gln
    610                 615                 620 ggg agc aca ata agc agt cct agt gaa atg gca cag gga atc aga gca         1920
Gly Ser Thr Ile Ser Ser Pro Ser Glu Met Ala Gln Gly Ile Arg Ala
625                 630                 635                 640 ggg aaa ata gct gaa gga aat gat gca cat tct ctt tct ctt caa gct         1968
Gly Lys Ile Ala Glu Gly Asn Asp Ala His Ser Leu Ser Leu Gln Ala
                645                 650                 655 gtt gaa act aga cag caa aca caa gtc atc aaa gtt gta cca cat aac         2016
Val Glu Thr Arg Gln Gln Thr Gln Val Ile Lys Val Val Pro His Asn
            660                 665                 670 cgg aaa tca gcg acg gaa tca gca gct aga att ttt caa tcc att caa         2064
Arg Lys Ser Ala Thr Glu Ser Ala Ala Arg Ile Phe Gln Ser Ile Gln
        675                 680                 685 gaa gag aga aaa caa cat gat tta gtc tag                                 2094
Glu Glu Arg Lys Gln His Asp Leu Val *
    690                 695

<210> SEQ ID NO 2
<211> LENGTH: 697
<212> TYPE: PRT
<213> ORGANISM: Glycine max

<400> SEQUENCE: 2

Met Lys Arg Gly Asn Glu Glu Lys Ser Ala Gly Pro Met Phe Pro
1               5                   10                  15

Arg Leu His Val Asn Asp Ala Glu Lys Gly Gly Pro Arg Ala Pro Pro
            20                  25                  30

Arg Asn Lys Met Ala Leu Tyr Glu Gln Phe Ser Ile Pro Ser Gln Arg
        35                  40                  45

Phe Asn Pro His Leu Pro Arg Lys Pro Asn Ser Ser Ser Asn Ile Val
    50                  55                  60

Pro Pro Pro Thr Ser Ser Thr Glu Gly Asn Gly Arg Glu Arg Ser Tyr
65                  70                  75                  80

Ile Ser Arg Gln Ser Asp Asp Gly Ala Arg Ser Asn Thr Ser Leu Val
                85                  90                  95

Gln Leu Glu Arg Arg Lys Lys Val Asp Asp Gly Ile His Val Tyr Thr
            100                 105                 110

Cys Ser Arg Ile Asp Gln Ser Asn Asp Lys Met Leu Glu Ser Phe Asn
        115                 120                 125

Gly Lys Lys Leu Thr Pro Phe Gly Ala Arg Asn Phe Cys Tyr Ser Val
    130                 135                 140

Ala Val Gln Asn Gly Gly Asp Lys Asp Thr Thr Gln Phe Gly Phe Leu
145                 150                 155                 160

Pro Ala Asp Met Arg Lys Asp Ala Arg Lys Gly Asn Glu Ala Asn Pro
                165                 170                 175

His Val Ser Ser Ser Arg Gln Lys Leu Lys Leu Ser Val Lys Pro Lys
            180                 185                 190

Ser Ser Gly Glu Ile Ile Asp Ser Leu Val Met Gln Ala Lys Val Ile
```

-continued

```
            195                 200                 205
Pro Asn Gln Glu Asp Gln Asp Tyr Ser Val Pro Asn Ile Asn Arg Leu
    210                 215                 220

His Gln Asp Asp Ala Cys Leu Gln Lys Glu Cys Val Ala Gly Ser Gln
225                 230                 235                 240

Ser Asn Asp Ile Glu His Gly Gly Asp Leu Leu Asn Ser Thr Arg Asp
                245                 250                 255

Met Asp Asn Gly Asn Ala Leu Val Pro Arg Gly Cys Phe His Ser Ala
            260                 265                 270

Ala Asn Gln Thr His Pro Leu Glu Ala Thr Asn Asp Ala Glu Tyr His
        275                 280                 285

Asp Thr Arg Thr Gly Gly Pro Ile Gln Lys Gly Asn Phe Asp Glu Ser
    290                 295                 300

Asp Asn Ile Ser Lys Ile Ser Thr Val Thr Asn Leu Ser Ser Leu Ile
305                 310                 315                 320

Val Ser Pro Asp Asp Val Val Gly Ile Leu Gly Gln Lys His Phe Trp
                325                 330                 335

Lys Ala Arg Arg Lys Ile Ala Asn Gln Gln Ser Val Phe Ala Val Gln
            340                 345                 350

Val Phe Glu Leu His Arg Leu Ile Lys Val Gln Gln Leu Ile Ala Ala
        355                 360                 365

Ser Pro Asp Val Leu Leu Glu Asp Gly Ala Phe Met Gly Lys Phe Pro
    370                 375                 380

Leu Met Gly Ser Pro Pro Lys Asn Lys Asn Ile Ser Leu Glu Val Val
385                 390                 395                 400

Val Glu Pro Gln Gln Gln Asn Pro Lys Gln Lys Asn Asp Ser Glu Lys
                405                 410                 415

Leu Asn His Lys Thr Glu Cys Ser Ala Glu Asn Ala Val Ala Lys Lys
            420                 425                 430

Lys Ser Phe Ser Ser Pro Lys Asn Gly Ser His His Thr Asn His Thr
        435                 440                 445

Pro Phe Ser Gly Thr Pro His Gln Ala Asn Glu Ala Ser Asp Asn Lys
    450                 455                 460

Thr Ser Pro Trp Cys Phe Asn Gln Ala Pro Gly His Gln Trp Leu Ile
465                 470                 475                 480

Pro Val Met Ser Pro Ser Glu Gly Leu Val Tyr Lys Pro Tyr Pro Gly
                485                 490                 495

Pro Gly Phe Met Gly Thr Met Asn Gly Gly Cys Gly Gly Pro Phe Gly
            500                 505                 510

Gln Ala Pro Leu Gly Ala Thr Phe Met Asn Pro Ala Tyr Gln Phe Pro
        515                 520                 525

Ala Ser His Pro Val Val Gly Val Ser Pro Phe Val Pro Pro Ala Ser
    530                 535                 540

His Ala Tyr Phe Pro Ser Phe Gly Met Pro Val Val Asn Gln Ala Thr
545                 550                 555                 560

Ser Gly Ser Thr Val Glu Gln Val Asn Gln Phe Ala Ala Gln Gly Ser
                565                 570                 575

His Gly Gln Asn Gly His Ser Tyr Ile Glu Gly Thr Asp Phe Asn Thr
            580                 585                 590

His His Asn Gln Ser Ser Ser Asn Leu Pro Val Leu Lys Asn Gly Ala
        595                 600                 605

Thr Leu His Val Lys Lys Ser Gln Ala Ser Lys Glu Arg Gly Leu Gln
    610                 615                 620
```

```
Gly Ser Thr Ile Ser Ser Pro Ser Glu Met Ala Gln Gly Ile Arg Ala
625                 630                 635                 640

Gly Lys Ile Ala Glu Gly Asn Asp Ala His Ser Leu Ser Leu Gln Ala
            645                 650                 655

Val Glu Thr Arg Gln Gln Thr Gln Val Ile Lys Val Pro His Asn
        660                 665                 670

Arg Lys Ser Ala Thr Glu Ser Ala Ala Arg Ile Phe Gln Ser Ile Gln
        675                 680                 685

Glu Glu Arg Lys Gln His Asp Leu Val
    690                 695

<210> SEQ ID NO 3
<211> LENGTH: 1728
<212> TYPE: DNA
<213> ORGANISM: Glycine max
<220> FEATURE:
<221> NAME/KEY: promoter
<222> LOCATION: (1)...(1728)

<400> SEQUENCE: 3
```

| | | | | | |
|---|---|---|---|---|---|
| cctcttttag | tgctatttaa | tgtccattaa | tggtttaaac | tatataccaa | tacgggtttc | 60 |
| ttctgtatac | tatttatgaa | aacgtattat | aagattaaaa | tattataaga | ttacaatatt | 120 |
| atttgattaa | atataccttc | tttatctgtg | tcagatatat | catcgatatc | tttctcctca | 180 |
| tctagcgagt | cctcaacata | tgaattagat | attatgtaat | cgtcattgtc | agaatcttca | 240 |
| tctaaatttt | ttgcaaatct | ttgaactttt | cattcattgc | cagctatatt | attcccacat | 300 |
| gataatagcg | aatttgtcac | gttcgatgca | gaagcaccga | caacatctac | ttcaacgcac | 360 |
| aattcaagga | cacccatttc | ttgttgttgt | tgaaaacttt | caatcattgt | ttcaacatct | 420 |
| tcatcgtcac | aaatttgcaa | tgcaatatat | ttacttgcaa | ctaaaaatcg | gcaagtcata | 480 |
| gtagatatac | tttcattttt | atctaatttt | accttatcat | gaattctttt | ttttaaccca | 540 |
| tcaaagtta | caccacgttt | aatttgaata | gtctttttag | gaccttcaaa | tctaatgccg | 600 |
| tcgtcacttt | caaatattct | tccattcaaa | taaaccagaa | caacaatcaa | agaactcatt | 660 |
| tttataataa | aacctacaga | ataattttc | attaacaata | ataacataaa | aaaaatccaa | 720 |
| attaataaaa | aaattaataa | atatattact | gattttcacc | acacaaaaga | aatatcaaca | 780 |
| aagttgtagt | atagagagaa | agaaatttgg | agagatgcga | aaatgtacta | gaaagtgtgt | 840 |
| ctgaatgtat | aggcatgtat | tgcgtcgata | gtaatggcgc | aatacattgt | acttaagtaa | 900 |
| tttgaccaca | gggttgctcc | aactgacatg | acacaataca | ttttcagctg | gtcacatgct | 960 |
| gccgaaagca | gtcaatactg | acagttaaca | ctacatacgc | taacatagtc | tgtccaaaag | 1020 |
| tgattgtgcc | accacagctg | tagcaaccca | ttgcgaaaaa | cttttgacac | aacaactcaa | 1080 |
| tgtcacatgt | cagtttccca | ttgaattgcg | ccctggcctt | tagcgcaatg | taaataaaaa | 1140 |
| caaaccctca | ataaatagtt | tgaaaacagt | catcttttag | taaataatttt | agaaaaggac | 1200 |
| tcctagtatt | tttgtcttaa | ttatacttaa | aaactcatta | ctcttcctta | gaatatagtt | 1260 |
| tgcagaatta | aactcagatc | atttcttata | aattaaatac | gtattctcaa | ctaaattaca | 1320 |
| tttattatta | ttagataaaa | aataaaaaat | ataaatgata | attagttaaa | attaatgtgg | 1380 |
| aatggataaa | gaaaagaaaa | ggaaagcgaa | caatctgggc | aagaaaatct | aatcatgtgt | 1440 |
| agagatatgt | cgtagtgggg | tccacaaaac | cgcactttt | ctatcttctc | tcacctcgga | 1500 |
| gccctgtctg | agaatcccta | actccgctgt | tccgtttccc | gtactttct | ttctgctgcc | 1560 |

| caatcttttt cttcacgtca actcctcctt cttattcttc ttccactttc tccatcttag | 1620 |
| attttttct ttcagattcg attcagatta tggtttttct tcttcttctt cttctctctc | 1680 |
| cttgtgcaaa ttgagataaa ataaagagaa aattgggata ataggatg | 1728 |

<210> SEQ ID NO 4
<211> LENGTH: 2010
<212> TYPE: DNA
<213> ORGANISM: Arabidopsis thaliana
<220> FEATURE:
<221> NAME/KEY: promoter
<222> LOCATION: (1)...(2010)
<223> OTHER INFORMATION: AtPyk-20 promoter sequence

<400> SEQUENCE: 4

| gccaccgagt attttgaact ccgaaatgat ttctcactat ccgaccactc ccaattatat | 60 |
| aacatgctta gaattattcg taagatggat cgtagttgca ttttacgaca ccatacagga | 120 |
| caagtccatg atagtttgag ttggtggatt ttggaacccc tgcaaattta ttttatacat | 180 |
| aacaaaggcc ccaatccatt ccttagcatc acaacttggg acttctatct tttgaaggat | 240 |
| acattcactt gttggttttg gtaaatatga ttgtttctttt acttccgaat aagcaatata | 300 |
| taaaagtatc taaaaacgga agtaactttt gatgatccta aaggttttgt aattgataca | 360 |
| tgtccaaaaa cctcttaata ttctttctca caaactgttg atggagttaa caaagggaga | 420 |
| caaggtaatt gggacaatat caacgttaga tacaggacaa gtgaaaaatg tggggttgat | 480 |
| gtcttcagct gcagcatatc accgttggta tatattgtca attattagtc ctatggatt | 540 |
| gaaacgtgtt ttagtaaata agagtgtcca agtgggacat ttccaataac gtatcacagc | 600 |
| tcctagagct tttgctatgt ttctctaggc ctgggccgcc tagcccacat tccaagcaag | 660 |
| gaaatgaatg gagttgggca tcaaaatttt ggaagcattt ttaagacaaa ttatctttta | 720 |
| agtttccttt tttaaacata aactatattt taggcttttt taagataaat attatttgga | 780 |
| ttttctttca ctcatatttt tggatttcaa cttaacaaaa catagggcgt gtctatttga | 840 |
| ctccacctac ccaccctact ggagttcgat cccactaaat cgcgttatcc cgcatagtag | 900 |
| ggattgacta tggatcggac tttgtcgatc caaagatatc taagaaattc agaaaagatt | 960 |
| gtataaaatt cagaaacgat tttacgaaat tcatgaaaaa tgagaaatac atgttttttt | 1020 |
| taatttacgt cggcattaaa aacgttggac cggctctgtg tttcaccaaa gaaattgttt | 1080 |
| cagtttatgc atgatcttca acttccatat tcttgttttc aattctggaa atccctaaca | 1140 |
| gatcggagct ctcctcattc agtgagttgg aagattgcat gattatataa ttactcttca | 1200 |
| catccacata tattcatta tattccccta taatttcata caaccctaga aaagaatctt | 1260 |
| caagtaatct aatcgtgtcg atgactccac tcatttgcta gaaagaaaa aacaaacaga | 1320 |
| cttcatttag ctgaaaacaa tcttttattc aacattacaa agcactgatc aaagaacctc | 1380 |
| taacatggta atatatctat gacattttac gtatcctaaa agaaaacaaa aagtgatgta | 1440 |
| ttggatgatg tttttttttt ttactttcta gtttcttatt acaacgacaa aaagagtcca | 1500 |
| cgtcgtcacg cacttttccg gtggtgaaaa aaatgtccaa atggattaaa tctataatat | 1560 |
| ctccagagag atcctctcct tctatctttt tgggctccac ttttcctatc tcttttttgcc | 1620 |
| cctttcctct ctctgttcac aagtcatctt cttccttcct ctgaatcttg ttcctttttg | 1680 |
| ctctctctac ttgattcacc cactctgttt ctcgattagt acgttgaaaa ctcactttgg | 1740 |
| ttttgtttga ttcctctttta gtctgttttt cgatttcgtt ttctctgatt ggtttggtgg | 1800 |
| tgagatctct atcgtagttt gtcctttggg ttaagatatt tcatttgatt ggtgggtttg | 1860 |

```
ttttattgaa gcttattgtt gtgaaagttg gagtctttct cagtttttag gttgaattat      1920
taagagaaag ggaagatttt tggtgtgaag ttaggttatt tggggtttga aagtttgca      1980 agtgaaaaag gttgtgaatt gtgagtgatg                                      2010

<210> SEQ ID NO 5
<211> LENGTH: 2494
<212> TYPE: DNA
<213> ORGANISM: Glycine max
<220> FEATURE:
<221> NAME/KEY: misc_feature
<222> LOCATION: (1)...(2494)
<223> OTHER INFORMATION: Complete sequence of soybean pyk20 cDNA clone

<400> SEQUENCE: 5
cgctgttccg tttcccgtac ttttctttct gctgcccaat cttttcttc acgtcaactc        60 ctccttctta ttcttcttcc actttctcca tcttagattt ttttctttca gattcgattc      120
agattatgct ttttcttctt cttcttcttc tctctccttg tgcaaattga gataaaataa      180
agagaaaatt gggataatag gatgaagaga gggaacgagg aagagaagtc ggcggggcca      240
atgttcccaa ggctgcatgt aaatgatgca gagaaaggag ggccaagagc accgccaagg      300
aacaagatgg ccctctatga acagttcagt attccatctc agaggttcaa tccacacctg      360
ccacgaaaac caaattcttc ttctaacata gttcctccac caacttcctc aactgaggga      420
aatggccgtg agagaagtta tatttctcgc caatctgatg atggagcaag gtcaaacact      480
tcattggtgc aacttgaacg gagaaaaaaa gtagatgatg cattcatgt gtacacttgc      540 tcgaggattg atcaatccaa tgataaaatg ctggagagtt ttaatgggaa aaaattgact      600 cctttggtg ctaggaattt tgttattca gttgctgtgc aaaatggtgg tgacaaggat      660
acaacacaat ttggcttcct tcctgctgat atgagaaag atgcgaggaa ggggaatgag      720
gcaaatccac atgtaagctc aagtagacag aaactaaaat tgtctgtcaa acccaaatca      780
agtggagaaa ttattgacag tctagtgatg caagccaagg tgattccaaa tcaagaggat      840
caagattatt ctgtgccaaa tataaacagg ttacatcagg atgatgcttg cctacagaag      900
gagtgtgtgg ctgggtccca atccaatgac atcgagcatg tggtgatct ccttaactct      960 acaagggata tggataatgg aaatgcgctc gtaccaagag gctgttttca ttctgcagcg     1020
aaccaaactc acccacttga ggctaccaat gatgctgaat atcacgatac tcggactgga     1080
ggcccgatac agaagggaa ttttgatgaa agtgacaaca tttccaagat ctccactgta     1140
acaaatttat caagtctgat agtttctcct gatgatgttg tagggatatt aggtcaaaaa     1200
catttctgga agcaagaag aaaaattgcc atcaacaga gtgtgtttgc agtccaagtg     1260
tttgaattgc acagactgat taaggtccaa cagctaattg ctgcatcacc ggatgttttg     1320
cttgaagatg gtgctttcat gggaaaattt cctttgatgg gttctcctcc taaaaataaa     1380
aatatctcat tggaagtggt tgtagagcct cagcaacaaa atcctaagca gaaaaacgat     1440
tctgaaaagc taaaccataa aacagaatgt tcagctgaga atgcagttgc gaaaaaaaaa     1500
tctttttcgt ccccgaaaaa tggtagccac catacaaatc acccccatt ttcaggaact     1560 ccacaccagg caaatgaagc ttctgataat aaaacaagtc cctggtgttt caatcaggca     1620
cctggacatc aatggttaat tcctgtcatg tctccttctg aagggcttgt ctacaagcca     1680
tatcctgggc ctggattat gggaacaatg aatggaggat gcggcgggcc attcgggcaa     1740
gcacctctcg gtgctacttt catgaatcct gcctatcaat tccagcttc tcatccagta     1800
```

-continued

```
gttggggttt caccgtttgt ccctccagcc agtcatgcct acttcccttc ctttggcatg    1860
ccagtagtga atcaagcaac atcaggatca actgttgaac aggtgaacca gtttgctgca    1920
caaggttctc atggtcaaaa tggtcattca tatatagagg gaaccgattt taacactcat    1980
cataaccaaa gctcatctaa cctgccagtt ctgaagaatg gagctacgct acatgttaaa    2040
aaatctcagg cgtctaagga gagagggtta caagggagca caataagcag tcctagtgaa    2100
atggcacagg gaatcagagc agggaaaata gctgaaggaa atgatgcaca ttctctttct    2160
cttcaagctg ttgaaactag acagcaaaca caagtcatca aagttgtacc acataaccgg    2220
aaatcagcga cggaatcagc agctagaatt tttcaatcca ttcaagaaga gagaaaacaa    2280
catgatttag tctagtgctg tttatggagg tggagttatt tgagttgatt ttgtacagtg    2340
cgtcaagtcc tgtactttgt tgttgtttgg taatatgtat cttgctgttt tattctactc    2400
ttcctttatg tccttttttct tacaacatat tcgaatgtag atattgttat aactacaatg    2460
gaatgttaaa attgatcaaa aaaaaaaaaa aaaa                                 2494

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 6
ctcttcctcg ttccctctct tcatccta                                          28

<210> SEQ ID NO 7
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 7
tgccaccgag tattttgaac tccg                                              24

<210> SEQ ID NO 8
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 8
gcatcattca catgaagccg agg                                               23

<210> SEQ ID NO 9
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 9
ttatgcgggc aacgtctggt atc                                               23

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide Primer
```

-continued

<400> SEQUENCE: 10
gcagcagttt catcaatcac cacg                                              24

<210> SEQ ID NO 11
<211> LENGTH: 702
<212> TYPE: PRT
<213> ORGANISM: Arabidopsis thaliana
<220> FEATURE:
<221> NAME/KEY: PEPTIDE
<222> LOCATION: (0)...(0)
<223> OTHER INFORMATION: Arabidopsis thaliana Pyk20

<400> SEQUENCE: 11

Met Lys Arg Gly Lys Asp Glu Glu Lys Ile Leu Glu Pro Met Phe Pro
1               5                   10                  15

Arg Leu His Val Asn Asp Ala Asp Lys Gly Gly Pro Arg Ala Pro Pro
                20                  25                  30

Arg Asn Lys Met Ala Leu Tyr Glu Gln Leu Ser Ile Pro Ser Gln Arg
            35                  40                  45

Phe Gly Asp His Gly Thr Arg Asn Ser Arg Ser Asn Asn Thr Ser Thr
    50                  55                  60

Leu Val His Pro Gly Pro Ser Ser Gln Pro Cys Gly Val Glu Arg Asn
65                  70                  75                  80

Leu Ser Val Gln His Leu Asp Ser Ser Ala Ala Asn Gln Ala Thr Glu
                85                  90                  95

Lys Phe Val Ser Gln Met Ser Phe Met Glu Asn Val Arg Ser Ser Ala
            100                 105                 110

Gln His Asp Gln Arg Lys Met Val Arg Glu Glu Asp Phe Ala Val
        115                 120                 125

Pro Val Tyr Ile Asn Ser Arg Arg Ser Gln Ser His Gly Arg Thr Lys
    130                 135                 140

Ser Gly Ile Glu Lys Glu Lys His Thr Pro Met Val Ala Pro Ser Ser
145                 150                 155                 160

His His Ser Ile Arg Phe Gln Glu Val Asn Gln Thr Gly Ser Lys Gln
                165                 170                 175

Asn Val Cys Leu Ala Thr Cys Ser Lys Pro Glu Val Arg Asp Gln Val
            180                 185                 190

Lys Ala Asn Arg Arg Ser Gly Gly Phe Val Ile Ser Leu Asp Val Ser
        195                 200                 205

Val Thr Glu Glu Ile Asp Leu Glu Lys Ser Ala Ser His Asp Arg
    210                 215                 220

Val Asn Asp Tyr Asn Ala Ser Leu Arg Gln Glu Ser Arg Asn Arg Leu
225                 230                 235                 240

Tyr Arg Asp Gly Gly Lys Thr Arg Leu Lys Asp Thr Asp Asn Gly Ala
                245                 250                 255

Glu Ser His Leu Ala Thr Glu Asn His Ser Gln Glu Gly His Gly Ser
            260                 265                 270

Pro Glu Asp Ile Asp Asn Asp Arg Glu Tyr Ser Lys Ser Arg Ala Cys
        275                 280                 285

Ala Ser Leu Gln Gln Ile Asn Glu Glu Ala Ser Asp Asp Val Ser Asp
    290                 295                 300

```
Asp Ser Met Val Asp Ser Ile Ser Ile Asp Val Ser Pro Asp Asp
305                 310                 315                 320

Val Val Gly Ile Leu Gly Gln Lys Arg Phe Trp Arg Ala Arg Lys Ala
                325                 330                 335

Ile Ala Asn Gln Gln Arg Val Phe Ala Val Gln Leu Phe Glu Leu His
                340                 345                 350

Arg Leu Ile Lys Val Gln Lys Leu Ile Ala Ala Ser Pro Asp Leu Leu
                355                 360                 365

Leu Asp Glu Ile Ser Phe Leu Gly Lys Val Ser Ala Lys Ser Tyr Pro
        370                 375                 380

Val Lys Lys Leu Leu Pro Ser Glu Phe Leu Val Lys Pro Pro Leu Pro
385                 390                 395                 400

His Val Val Lys Gln Arg Gly Asp Ser Glu Lys Thr Asp Gln His
                405                 410                 415

Lys Met Glu Ser Ser Ala Glu Asn Val Val Gly Arg Leu Ser Asn Gln
                420                 425                 430

Gly His His Gln His Pro Thr Thr Cys Leu Phe Gln Gln Thr Thr His
                435                 440                 445

Arg Leu His Arg Leu Gln Met Asp Ile Ala Phe Leu Leu Ser Leu Leu
        450                 455                 460

Leu Gln Glu Ile Ile Ser Asn Gly Asp Pro Cys Asn Val Ser Leu Gly
465                 470                 475                 480

Arg Thr Asp Ile Gln Pro His Pro Gly Met Ala His Thr Gly His Tyr
                485                 490                 495

Gly Gly Tyr Tyr Gly His Tyr Met Pro Thr Pro Met Val Met Pro Gln
                500                 505                 510

Tyr His Pro Gly Met Gly Phe Pro Pro Gly Asn Gly Tyr Phe Pro
        515                 520                 525

Pro Tyr Gly Met Met Pro Thr Ile Met Asn Pro Tyr Cys Ser Ser Gln
        530                 535                 540

Gln Gln Gln Gln Gln Gln Pro Asn Glu Gln Met Asn Gln Phe Gly His
545                 550                 555                 560

Pro Gly Asn Leu Gln Asn Thr Gln Gln Gln Gln Arg Ser Asp Asn
                565                 570                 575

Glu Pro Ala Pro Gln Gln Gln Gln Pro Thr Lys Ser Tyr Pro Arg
                580                 585                 590

Ala Arg Lys Ser Arg Gln Gly Ser Thr Gly Ser Ser Pro Ser Gly Pro
        595                 600                 605

Gln Gly Ile Ser Gly Ser Lys Ser Phe Gly Pro Phe Ala Ala Val Asp
610                 615                 620

Glu Asp Ser Asn Ile Asn Asn Ala Pro Glu Gln Thr Met Thr Thr Thr
625                 630                 635                 640

Thr Thr Thr Thr Arg Thr Thr Val Thr Gln Thr Thr Arg Asp Gly Gly
                645                 650                 655

Gly Val Thr Arg Val Ile Lys Val Val Pro His Asn Ala Lys Val Val
                660                 665                 670

Pro His Asn Ala Lys Leu Ala Ser Glu Asn Ala Ala Arg Ile Phe Gln
        675                 680                 685

Ser Ile Gln Glu Glu Arg Lys Arg Tyr Asp Ser Ser Lys Pro
690                 695                 700
```

ISOLATED NEMATODE REGULATED GENE PROMOTER AND USE THEREOF

CROSS-REFERENCE TO RELATED APPLICATIONS

This application claims priority to and benefit of U.S. Provisional Application No. 60/467,623, filed May 2, 2003.

FIELD OF THE INVENTION

The invention relates to compositions and methods useful in creating or enhancing pathogen resistance in plants. Additionally, the invention relates to plants and other organisms which have been genetically transformed with the compositions of the invention.

BACKGROUND OF THE INVENTION

Plants are continually attacked by a diverse range of phytopathogenic organisms. These organisms cause substantial losses to crops each year. Traditional approaches for control of plant diseases have been the use of chemical treatment and the construction of interspecific hybrids between resistant crops and their wild-type relatives as sources of resistant germplasm. However, environmental and economic concerns make chemical pesticides undesirable, while traditional interspecific breeding is inefficient and often cannot eliminate the undesired traits of the wild species. Thus, the discovery of pest and pathogen-resistant genes provides a new approach to control plant disease.

Nematode infection is a significant problem in the farming of many agriculturally significant crops. For example, soybean cyst nematode (*Heterodera glycines*, herein referred to as "SCN") is a widespread pest that causes substantial damage to soybeans every year. Such damage is the result of the stunting of the soybean plant caused by the cyst nematode. The stunted plants have smaller root systems, show symptoms of mineral deficiencies in their leaves, and wilt easily. SCN is believed to be responsible for yield losses in soybeans that are estimated to be in excess of $500 million per year. Other pathogenic nematodes of significance to agriculture include the potato cyst nematodes, *Globodera rostochiensis* and *Globodera pallida*, which are key pests of the potato, while the beet cyst nematode *Heterodera schachtii* is a major problem for sugar beet growers in Europe and the United States.

The primary method of controlling nematodes has been through the application of highly toxic chemical compounds. The widespread use of chemical compounds poses many problems with regard to the environment because of the non-selectivity of the compounds and the development of pest resistance to the chemicals. Nematicides such as Aldicarb™, carbamate pesticide, and its breakdown products are known to be highly toxic to mammals. As a result, government restrictions have been imposed on the use of these chemicals. Thus, there is a great need for effective, non-chemical methods and compositions for nematode control.

Various approaches to pest control have been tried including the use of biological organisms which are typically "natural predators" of the species sought to be controlled. Such predators may include other insects, fungi, and bacteria such as *Bacillus thuringiensis*. Alternatively, large colonies of insect pests have been raised in captivity, sterilized and released into the environment in the hope that mating between the sterilized insects and fecund wild insects will decrease the insect population. While these approaches have had some success, they entail considerable expense and present several major difficulties. For example, it is difficult both to apply biological organisms to large areas and to cause such living organisms to remain in the treated area or on the treated plant species for an extended time. Predator insects can migrate and fungi or bacteria can be washed off of a plant or removed from a treated area by rain. Consequently, while the use of such biological controls has desirable characteristics and has met with some success, in practice these methods have not achieved the goal of controlling nematode damage to crops.

Advances in biotechnology in the last two decades have presented new opportunities for pest control through genetic engineering. In particular, advances in plant genetics coupled with the identification of insect growth factors and naturally-occurring plant defensive compounds or agents offer the opportunity to create transgenic crop plants capable of producing such defensive agents and thereby protect the plants against insect attack and resulting plant disease.

Transgenic plants that are resistant to specific insect pests have been produced using genes encoding *Bacillus thuringiensis* (Bt) endotoxins or plant protease inhibitors (PIs). Transgenic plants containing Bt endotoxin genes have been shown to be effective for the control of some insects. Effective plant protection using transgenically inserted PI genetic material has not yet been demonstrated in the field. While cultivars expressing Bt genes may presently exhibit resistance to some insect pests, resistance based on the expression of a single gene might eventually be lost due to the evolution of Bt resistance in the insects. Thus, the search for additional genes which can be inserted into plants to provide protection from insect pests is needed.

Additional obstacles to pest control are posed by certain pests. For example, it is known that certain nematodes, such as SCN, can inhibit certain plant gene expression at the nematode feeding site. Thus, in implementing a transgenic approach to pest control, an important factor is to increase the expression of desirable genes in response to pathogen attack. Consequently, there is a continued need for the controlled expression of genes deleterious to pests in response to plant damage.

One promising method for nematode control is the production of transgenic plants that are resistant to nematode infections. For example, with the use of nematode-inducible promoters, plants can be genetically altered to express nematicidal proteins in response to exposure to nematodes. See, for example, U.S. Pat. No. 6,252,138, herein incorporated by reference. Alternatively, some methods use a combination of both nematode-inducible and nematode-repressible promoters to obtain nematode resistance. Thus, WO 92/21757, herein incorporated by reference, discusses the use of a two-promoter system for disrupting nematode feeding sites where one nematode-inducible promoter drives expression of a toxic product that kills the plant cells at the feeding site while the other nematode-repressible promoter drives expression of a gene product that inactivates the toxic product of the first promoter under circumstances in which nematodes are not present, thereby allowing for tighter control of the deleterious effects of the toxic product on plant tissue. Similarly, with the use of proteins having a deleterious effect on nematodes, plants can be genetically altered to express such deleterious proteins in response to nematode attack.

Although these methods have potential for the treatment of nematode infections, their effectiveness is heavily dependent upon the characteristics of the nematode-inducible or nematode-repressible promoters discussed above, as well as, the deleterious properties of the proteins thereby expressed. Thus, such factors as the strength of such nematode-responsive promoters, degree of induction or repression, tissue specificity, or the like can all alter the effectiveness of these disease resistance methods. Similarly, the degree of toxicity and specificity of a gene product to nematodes, the protein's longevity after consumption by the nematode, or the like can alter the degree to which the protein is useful in controlling nematodes. Consequently, there is a continued need for the identification of nematode-responsive promoters and nematode-control genes for use in promoting nematode resistance.

SUMMARY OF THE INVENTION

Compositions and methods for promoting nematode and other pest resistance in plants are provided. The compositions include nucleic acid molecules comprising a sequence useful in nematode control operably linked to a nematode-regulated promoter, specifically a soybean Pyk20 promoter described herein, as well as vectors and transformed plant cells, plants, and seeds comprising these constructs. The nematode control sequences include Pyk20 proteins. Polynucleotides having nucleic acid sequences encoding Pyk20 polypeptides are provided. Also provided are purified Pyk20 proteins. The DNA sequences encoding these proteins can be used to transform plants, bacteria, fungi, yeasts, and other organisms for the control of pests.

In one aspect, this invention relates to DNA sequences isolated from soybean and *Arabidopsis*. These sequences alone, or in combination with other sequences, can be used to improve the nematode resistance of a plant. In another aspect of the present invention, expression cassettes and transformation vectors comprising the isolated nucleotide sequences are disclosed. The transformation vectors can be used to transform plants and express the nematode resistance genes in the transformed cells. In this manner, the nematode resistance of plants can be improved. Transformed cells, as well as, regenerated transgenic plants and seeds containing and expressing the isolated DNA sequences and protein products are also provided.

Embodiments of the invention include, but are not limited to, a nucleic acid molecule comprising a heterologous nematode-resistance sequence operably linked to a promoter that drives expression a heterologous nematode-resistance sequence in a plant cell, wherein said promoter comprises a nucleotide sequence selected from the group consisting of:
 (a) a nucleotide sequence comprising the sequence set forth in SEQ ID NO:3;
 (b) a nucleotide sequence comprising the sequence deposited as Patent Deposit No. PTA-4028
 (c) a nucleotide sequence comprising at least 20 contiguous nucleotides of the sequence of SEQ ID NO:3, wherein said nucleotide sequence has nematode-regulated promoter activity; and
 (d) a nucleotide sequence having at least 70% sequence identity to the sequence of SEQ ID NO:3, wherein said nucleotide sequence has nematode-regulated promoter activity.

Further embodiments of the invention include, but are not limited to, vectors comprising the promoter of SEQ ID NO: 3 and functional variants or fragments thereof, and dicot or monocot plants and plant cells having stably incorporated the promoter or its functional variants or fragments.

Another embodiment of the invention is a method of modulating the expression of a nucleotide sequence of interest, comprising stably incorporating into the genome of a plant cell a nucleotide sequence of interest operably linked to the promoter of SEQ ID NO:3 or functional fragments or variants thereof.

Another embodiment of the invention is a nucleic acid molecule comprising a first nucleotide sequence which comprises a heterologous nematode-resistance sequence, and which is operably linked to a first promoter capable of inducing transcription of the heterologous nematode-resistance sequence in a plant cell. The embodiment also comprises a second nucleotide sequence, which comprises a sequence capable of inhibiting the heterologous nematode-resistance sequence, and which is operably linked to a second promoter, which in turn is capable of repressing transcription of the inhibitor of the heterologous nematode-resistance sequence in a plant cell. In this embodiment, the first promoter comprises the nucleotide sequence of SEQ ID NO:3, or functional fragments or variants thereof. Expression cassettes comprising this nucleic acid molecule, and dicot or monocot plant cells having stably incorporated this nucleic acid molecule are also embodiments of the invention.

A further embodiment of the invention is a monocot or dicot plant stably transformed with a nucleic acid molecule comprising a heterologous nematode-resistance sequence operably linked to a promoter that induces transcription of the nematode-resistance sequence in a plant cell in response to a nematode stimulus, wherein said promoter comprises the nucleotide sequence of SEQ ID NO:3, or functional fragments or variants thereof. Seeds of this plant which comprise the nucleic acid molecule are also embodiments of the invention.

Another embodiment of the invention is a method for conferring or improving nematode resistance in a monocot or dicot plant comprising transforming a plant with a nucleic acid molecule comprising a heterologous sequence operably linked to a promoter that induces transcription of the heterologous sequence in a plant cell in response to a nematode stimulus and regenerating stably transformed plants, wherein the promoter comprises the nucleotide sequence of SEQ ID NO:3, or functional fragments or variants thereof.

The invention embodiments further include isolated polypeptides, the expression of which is induced in response to nematode infection, and comprising the amino acid sequence of SEQ ID NO: 2, a polypeptide encoded by a nucleotide sequence comprising the sequence set forth in SEQ ID NO:1, a polypeptide comprising an amino acid sequence encoded by a nucleotide sequence deposited as Patent Deposit No. PTA-4028, and fragments and variants of the aforementioned polypeptides. Further embodiments include nucleic acid molecules encoding such polypeptides, including the nucleic acid sequence of SEQ ID NO: 1, a nucleic acid molecule comprising the coding region of the sequence of SEQ ID NO:5, a nucleic acid molecule comprising a sequence encoding the amino acid sequence of SEQ ID NO:2, a nucleic acid molecule comprising a sequence deposited as Patent Deposit No. PTA-4028, and fragments or variants of these aforementioned nucleic acid molecules. Nucleotide constructs comprising these sequences are also embodiments of the invention, as well as methods for modulating the expression of a peptide of interest comprising transforming a host cell with these nucleic acid molecules.

Another embodiment of the invention is a transformed monocot or dicot plant or plant cell having stably incorporated into its genome at least one nucleotide construct comprising a nucleic acid molecule operably linked to a heterologous promoter that drives expression in the cell, wherein the nucleic acid molecule encodes a polypeptide which is induced during nematode infection and is a member of the Pyk20 gene family, including those comprising the amino acid sequence of SEQ ID NO: 2, a polypeptide encoded by a nucleotide sequence comprising the sequence set forth in SEQ ID NO:1, a polypeptide comprising an amino acid sequence encoded by a nucleotide sequence deposited as Patent Deposit No. PTA-4028, and fragments and variants of the aforementioned polypeptides. The heterologous promoter of these embodiments may be, but is not limited to, a constitutive promoter, a tissue-preferred promoter, or an inducible promoter.

Another embodiment of the invention is a nucleotide construct comprising a promoter which confers the ability to regulate transcription and which comprises the nucleic acid molecule sequence of SEQ ID NO:3, a nucleic acid molecule comprising the sequence deposited as Patent Deposit No. PTA-4028, or fragments and variants thereof. Expression vectors containing this construct are also embodiments of the invention.

A further embodiment of the invention is a method for conferring or improving nematode resistance of a plant, comprising stably introducing into the genome of a plant at least one nucleotide construct comprising a nucleic acid molecule operably linked to a heterologous promoter that drives expression in a plant cell, wherein the nucleic acid molecule encodes a polypeptide, the expression of which is induced in response to nematode infection, such as the nucleic acid molecule comprising the sequence of SEQ ID NO: 1, a nucleic acid molecule comprising the coding region of the sequence of SEQ ID NO:5, a nucleic acid molecule comprising a sequence encoding the amino acid sequence of SEQ ID NO:2, a nucleic acid molecule comprising a sequence deposited as Patent Deposit No. PTA-4028, and fragments, variants, and antisense sequences of these nucleic acid molecules.

BRIEF DESCRIPTION OF THE DRAWINGS

FIG. 1 shows the alignment of the amino acid sequences encoded by the soybean Pyk20 gene (SEQ ID NO: 2) and the *Arabidopsis* Pyk20 gene (Y11994) (SEQ ID NO: 11).

FIG. 2 shows GUS activity levels in transgenic soybean hairy roots containing SoyPyk20::GUS constructs (i.e., constructs in which the soybean Pyk20 promoter is operably linked to and thus drives expression of the GUS gene).

DETAILED DESCRIPTION OF THE INVENTION

The present invention provides, inter alia, compositions and methods for promoting pathogen resistance in plants, more particularly for improving nematode resistance of susceptible plants. The compositions of the invention are nucleic acid molecules comprising sequences useful in improving nematode resistance in plants. These compositions can be transferred into plants to confer or improve nematode resistance in the transformed plants. By "confer or improve nematode resistance" it is intended that the proteins or sequences, either alone or in combination with other proteins or sequences, enhance resistance of a plant to nematodes and nematode-caused damage. In this manner, resistance to nematodes can be enhanced or improved in the transformed plant when at least one of the sequences of the invention is provided.

The compositions comprise nucleic acid molecules comprising sequences of plant genes and the polypeptides encoded thereby. Particularly, the nucleotide and amino acid sequences for a soybean Pyk20 gene (SEQ ID NOs: 1 and 2) are provided. As discussed in more detail below, the sequences of the invention are involved in many basic biochemical pathways that regulate plant stress responses, development, metabolism, and pathogen resistance. Thus, methods are provided for the expression of these sequences in a host plant to modulate plant stress responses, developmental pathways, metabolism, and defense responses. Some of the methods involve stably transforming a plant with a nucleotide sequence capable of modulating the plant's metabolism operably linked with a promoter capable of driving expression of a gene in a plant cell.

The compositions also comprise nucleic acid molecules comprising sequences useful in the control of gene expression in improving nematode resistance. Particularly, provided are soybean Pyk20 promoter and *Arabidopsis* Pyk20 promoter sequences set forth in SEQ ID NO: 3 and SEQ ID NO:4, respectively. Also provided are the transcribed but untranslated regions of the soybean Pyk20 gene set forth in SEQ ID NO:5, which may contain regulatory elements. Methods are provided for the regulated expression of a nucleotide sequence of interest that is operably linked to the Pyk20 promoter sequences disclosed herein. Nucleotide sequences operably linked to the Pyk20 promoter are transformed into a plant cell. Exposure of the transformed plant to a stimulus induces transcriptional activation of the nucleotide sequences operably linked to the Pyk20 promoter.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

The Pyk20 promoter sequences may find use in the regulated expression of an operably linked heterologous gene of interest. For example, the provided sequences may find use as a nematode-regulated promoter, such as a nematode-inducible promoter. In addition to these promoter sequences, the nematode-regulated promoters of the invention encompass fragments and variants of these particular promoters as defined herein. Thus, a fragment of the promoter sequence provided in SEQ ID NO:3 may be used either alone or in combination with other sequences to create synthetic promoter constructs. In such embodiments, the fragments (also called "elements" or "subsequences") confer desired properties on the synthetic promoter construct, such as conferring increased transcription of operably linked sequences in response to stress caused by nematode attack.

By "nematode-regulated" promoter, a promoter whose transcription initiation activity is either induced or repressed in response to a nematode stimulus is intended. Thus, a nematode-inducible promoter increases expression of an operably linked nucleotide sequence in the presence of a nematode stimulus. In contrast, a nematode-repressible promoter decreases the transcription of an operably linked nucleotide sequence in the presence of a nematode stimulus. Nematode-repressible promoters provide a means for improved regulation of genetically engineered nematode resistance in plants. It is known that expression of a toxin gene product at nematode feeding sites can potentially harm uninfected plant cells in tissues adjacent to those sites. Thus, it can be beneficial to additionally alter the transgenic plant to express a product that counteracts excessive production of the toxin. See, for example, the methods disclosed in WO 92/21757.

Thus, in another embodiment of the invention, a nematode-repressible promoter is used in combination with a nematode-inducible promoter, such as a Pyk20 promoter of the present invention, to effect improved regulation of nematode resistance in a plant. In this manner, two transgene units in one or two nucleic acid molecules are used in concert to transform plant cells and regenerate transgenic plants having improved nematode resistance with respect to nontransgenic plants of the same species. The first transgene unit comprises a nematode-inducible promoter operably linked to a nematode-resistance sequence. The second nucleic acid molecule comprises a nematode-repressible promoter operably linked to a heterologous nucleotide sequence that encodes a gene product that, when expressed in a plant cell, inhibits or inactivates a toxic product of a nematode-resistance gene (i.e., the toxic product encoded by the first nucleic acid molecule) that has been engineered within the plant cell. Such products are referred to herein as "nematode-resistance inhibitor products," and their coding sequences are referred to herein as "nematode-resistance inhibitor sequences." In response to a nematode stimulus, expression of the nematode-resistance sequence allows for production of the toxin at the point of nematode invasion, while inhibition or repression of the expression of the nematode-resistance inhibitor product of the second nucleic acid molecule allows for the toxin to accumulate within the infected cells. In the absence of the nematode stimulus, such as in adjacent uninfected cells, expression of the inhibitor product of the second nucleic acid molecule protects against any aberrant accumulation of the toxin within these adjacent cells. Similarly, following removal of the nematode stimulus from an infected region, upregulation of expression of the inhibitor product encoded by the second nucleic acid molecule protects the remaining cells within the invasion region against the toxic effects of any residual toxin. For example, the SCP1 promoter has strong and constitutive activity in various plant tissues, as described more fully in U.S. Pat. No. 6,072,050, but its activity can be significantly repressed in nematode feeding sites. These features of the SCP1 promoter make it a useful choice for de-repressing a nematode-resistance inhibitor transgene in comparison to a constitutive promoter, as described more fully in WO 92/21757, in terms of improving nematode resistance. Examples of nematode-resistance inhibitor products that might be useful in such an embodiment when regulated by the nematode-repressible promoter include, but are not limited to, barstar, which neutralizes the activity of barnase; EcoRI methylase, which targets the endonuclease EcoRI; protease inhibitors targeting proteases, such as papain; and an antisense RNA complementary to a strand of sense RNA encoded by the toxic gene sequence of the first nucleic acid molecule.

When using a nematode-inducible or nematode-repressible promoter, expression of the operably linked nucleotide sequence is initiated or inhibited, respectively, in cells in response to a nematode stimulus. As used herein, "nematode stimulus" refers to a nematode-derived agent capable of acting as a stimulus to initiate or repress nematode-regulated promoter activity as described herein. "Nematode stimulus" is contemplated to include nematodes and fragments thereof, such as proteins, nucleic acids, cell wall components, and the like, as would be known to the skilled artisan to act as a stimulus for a nematode-inducible or nematode-repressible promoter. Nematode stimulus also includes a signal resulting from nematode infection, wounding, and the like. For example, proteins, nucleic acids, secondary metabolites, peptides, chemicals, and the like, released during nematode parasitism or released as a result of nematode wounding, fall within the definition of nematode stimulus contemplated herein.

"Nematodes," as defined herein, refer to parasitic nematodes such as cyst, root-knot, and lesion nematodes, including *Heterodera* spp, *Meloidogyne* spp., *Globodera* spp. and *Pratylenchus* spp., particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Other examples of nematodes contemplated in the present invention are given elsewhere herein.

Thus, the nematode-inducible sequences disclosed herein, when assembled within a nucleic acid molecule such that the promoter is operably linked to a heterologous nucleotide sequence of interest, enable expression or repression (inhibition) of expression of the heterologous nucleotide sequence in the cells of a plant stably transformed with this nucleic acid molecule. By "heterologous nucleotide sequence" a sequence that is not naturally occurring with the promoter sequence is intended. While this nucleotide sequence is heterologous to the promoter sequence, it may be homologous, or native, or heterologous, or foreign, to the plant host. By "operably linked" a functional linkage between a promoter and a second sequence, wherein the promoter sequence initiates and mediates transcription of the DNA sequence corresponding to the second sequence is intended. Generally, operably linked means that the nucleic acid sequences being linked are contiguous and, where necessary to join two protein coding regions, contiguous and in the same reading frame.

The type of nucleotide sequence within a nucleic acid molecule of the present invention depends upon its intended use. Thus, when the nucleic acid molecule comprises a nematode-inducible promoter, it is of interest to operably link that promoter to a nucleotide sequence useful in improving pathogen resistance, more particularly, in improving nematode resistance. Such sequences are referred to herein as "nematode-resistance sequences." By "nematode-resistance sequence" a sequence coding for an RNA and/or a protein or polypeptide that, when expressed, either inhibits, prevents, or repels nematode infection or invasion of a plant cell, thereby limiting the spread and reproduction of the nematode is intended. Such sequences include sequences encoding nematode-resistance proteins and cytotoxic proteins or polypeptides that disrupt cell metabolism, the byproducts of which are essential for nematode survival and/or reproduction. Expression of such sequences allows a plant to avoid the disease symptoms associated with nematode infection, or prevent or minimize nematodes from causing disease and associated disease symptoms. These sequences may function as nematicides, that is as nematode-killing sequences. Such killing may occur by direct action on nematodes, or by action on the cells of the plant on which the nematodes feed to kill those cells, thereby depriving the infecting nematodes of a site of entry or of feeding. Alternatively, such nematicides may act on other surrounding tissue to cause the release of nematode toxins from those tissues. Such nematode-resistance sequences are provided in, for example, U.S. Pat. Nos. 5,750,386; 5,994,627; 6,006,470; and 6,228,992, incorporated herein by reference. Other examples of nematode resistance genes include Oryzacystatin-1 and cowpea trypsin inhibitor (Urwin et al. (1998) *Planta* 204: 472–479); Rhg (Webb et al. (1995) *Theor. Appl. Genet* 91: 574–581); Hs1 (Cai et al. (1997) *Science* 275: 832–834); and CRE3 (Lagudah et al. (1997) *Genome* 40: 650–665); all of which are herein incorporated by reference.

Examples of nematode-resistance sequences that code for substances that are cytotoxic to plants include, but are not limited to, enzymes capable of degrading nucleic acids (DNA and RNA) such as nucleases, restriction endonucleases (such as EcoRI), micrococcal nucleases, RNase A, and barnase (i.e., mature *Bacillus amyloliquefaciens* RNase; see Mariani et al. (1990) *Nature* 347: 737–741 and Paddon et al. (1985) *Gene* 40: 231–39); enzymes which attack proteins such as proteases, including but not limited to, trypsin, pronase A, carboxypeptidase, endoproteinase Asp-N, endoproteinase Glu-C, and endoproteinase Lys-C; ribonucleases such as RNase CL-3 and RNase $T_1$; toxins from plant pathogenic bacteria such as phaseolotoxin, tabtoxin, and syringotoxin; lipases such as those produced from porcine pancreas and *Candida cyclindracea*; membrane channel proteins such as glp F and connexins (gap junction proteins), and antibodies which bind proteins in the cell so that the cell is thereby killed or debilitated.

Genes that produce antibodies to plant cell proteins can be produced as described in Huse et al. (1989) *Science* 246: 1275–1281. Proteins to which such antibodies can be directed include, but are not limited to, RNA polymerase, respiratory enzymes, cytochrome oxidase, Krebs cycle enzymes, protein kinases, aminocyclopropane-1-carboxylic acid synthase, and enzymes involved in the shikimic acid pathway such as enolpyruvyl shikimic acid-5-phosphate synthase. In one embodiment, the toxic product is a structural gene encoding mature *Bacillus amyloliquefaciens* RNase (or Barnase). See, e.g., Mariani et al. (1990) *Nature* 347: 737–741 and Paddon et al., (1985) *Gene* 40: 231–239. The toxic product may either kill the plant cell in which it is expressed or simply disable the cell so that it is less capable of supporting the pathogen. Where the plant is a food plant, the plant-toxic product may be non-toxic to animals and/or humans.

Structural genes employed in carrying out the present invention encode a product which is toxic to nematodes. A wide variety of protein or peptide products which are toxic to plant cells can be used in the present invention, including but not limited to, proteinase inhibitors; defensins; enzymes which attack proteins, such as trypsin, pronase A, carboxypeptidase, endoproteinase Asp-N, endoproteinase Glu-C, and endoproteinase Lys-C; ribonucleases such as RNase CL-3 and RNase $T_1$; toxins from plant pathogenic bacteria such as phaseolotoxin, tabtoxin, and syringotoxin; lipases such as those produced from porcine pancreas and *Candida cyclindracea*; and any other anti-nematode peptide; and antibodies which bind proteins in the cell so that the cell is thereby killed or debilitated.

Genes that produce antibodies to nematode cell proteins can be produced by methods known in the art. Proteins to which such antibodies can be directed include, but are not limited to, parasitic factors and other proteins secreted by nematodes to facilitate feeding site induction.

Where the expression product of the structural gene is to be located in a cellular compartment other than the cytoplasm, the structural gene may be constructed to include regions which code for particular amino acid sequences which result in translocation of the product to a particular site, such as the cell plasma membrane, or may be secreted into the periplasmic space or into the external environment of the cell. Various secretory leaders, membrane integration sequences, and translocation sequences for directing the peptide expression product to a particular site are described in the literature. See, for example, Cashmore et al. (1985) *Bio/Technology* 3: 803–808 and Wickner et al., (1985) *Science* 230: 400–407.

Nucleic acid sequences encoding gene products useful in improving resistance to nematodes are provided. Particularly, a nucleic acid sequence encoding a Pyk20 protein from soybean is provided. The soybean Pyk20 sequence shares about 46% homology to the previously disclosed *Arabidopsis* Pyk20 gene. See, for example, Puzio et al. (1999) *Gene* 239: 163–72, entitled, "Isolation of a gene from *Arabidopsis thaliana* related to nematode feeding structures." The Pyk20 nomenclature is being used to describe the gene and promoter sequences isolated from soybean because of their homology to the previously disclosed *Arabidopsis* Pyk20 gene, which is clearly from the same family. Therefore, the abbreviation "Pyk" does not have a particular meaning and is not being used as an acronym.

The Pyk20 promoter and gene are part of the plant's response to attack by nematodes. While not wishing to be bound by any one theory, the sequences of the invention find use in controlling or modulating gene expression in response to nematode attack. Transformed plants can be obtained having altered or enhanced responses to nematode attack; hence, the methods and compositions find uses in altering the defense response of plants. Thus, the sequences of the invention find use in engineering broad-spectrum disease and pest resistance in a variety of plants. A polypeptide is said to belong to the Pyk20 gene family when it has one or more of the properties of the native Pyk20 protein including, but not limited to, causing an altered defense response, a response to nematode attack, modulating plant stress responses, modulating plant developmental pathways, and modulating plant metabolism. It is within the skill in the art to assay protein activities obtained from various sources to determine whether the properties of the proteins are the same. In so doing, one of skill in the art may employ any of a wide array of known assays including, for example, biochemical and/or pathological assays. For example, one of skill in the art could readily produce a plant transformed with a Pyk20 polypeptide variant and assay a property of the native Pyk20 protein in that plant material to determine whether a particular Pyk20 property was retained by the variant.

The compositions and methods of the invention find use in the activation or modulation of expression of other genes, including those involved in other aspects of nematode or other stress responses. For example, in one embodiment of the invention, the soybean Pyk20 promoter may be used to drive expression of an insecticidal protein which is accordingly induced in response to wounding or damage to the root tissue.

Although there is some conservation among Pyk20 genes, proteins encoded by members of this gene family may contain different elements or motifs or sequence patterns that modulate or affect the activity, subcellular localization, and/or target of the protein in which they are found. Such elements, motifs, or sequence patterns may be useful in engineering novel enzymes for modulating gene expression in particular tissues. By "modulating" or "modulation" it is intended that the level of expression of a gene may be increased or decreased relative to genes driven by other promoters or relative to the normal or uninduced level of the gene in question.

The expression of the Pyk20 gene has been shown to be induced in response to nematode infection. Expression of the proteins encoded by the sequences of the invention can be used to modulate or regulate the expression of proteins in these stress-response pathways related to nematode infection and the expression of proteins in other directly or indirectly affected pathways. Hence, the compositions and methods of the invention find use in altering plant response to the environment and environmental stimuli. In other embodiments, fragments of the Pyk20 gene are used to confer desired properties upon synthetic protein constructs for use in regulating plant growth or cellular processes, such as root growth.

The present invention provides for isolated nucleic acid molecules comprising nucleotide sequences encoding the amino acid sequence shown in SEQ ID NO:2 or the polypeptide-encoding nucleotide sequences of the nucleic acid molecules deposited in a bacterial host as Patent Deposit No. PTA-4028. Further provided are polypeptides having an amino acid sequence encoded by a nucleic acid molecule described herein, for example those polypeptides comprising the sequences set forth in SEQ ID NO:2 or those deposited in a bacterial host as Patent Deposit No. PTA-4028, and fragments and variants thereof.

The present invention further provides for an isolated nucleic acid molecule comprising the sequences shown in SEQ ID NO:1 or the promoter nucleotide sequences deposited in a bacterial host as Patent Deposit No. PTA-4028.

Plasmids containing the nucleotide sequences of the invention were deposited with the Patent Depository of the American Type Culture Collection (ATCC), 10801 University Boulevard, Manassas, Va., 20110-2209 on Feb. 1, 2002 and assigned Patent Deposit No. PTA-4028. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

The invention encompasses isolated or substantially purified nucleic acid or protein compositions. An "isolated" or "purified" nucleic acid molecule or protein, or a biologically active portion thereof, is substantially free of other cellular material, or culture medium when produced by recombinant techniques, or substantially free of chemical precursors or other chemicals when chemically synthesized. In some embodiments, an "isolated" nucleic acid is free of sequences (such as other protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.4 kb, 0.3 kb, 0.2 kb, or 0.1 kb, or 50, 40, 30, 20, or 10 nucleotides that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, culture medium may represent less than about 30%, 20%, 10%, or 5% (by dry weight) of chemical precursors or non-protein-of-interest chemicals.

Fragments and variants of the disclosed nucleotide sequences are encompassed by the present invention. Fragments and variants of proteins encoded by the disclosed nucleotide sequences are also encompassed by the present invention. By "fragment" a portion of the nucleotide sequence or a portion of the amino acid sequence and hence the protein encoded thereby is intended. Fragments of a nucleotide sequence may encode protein fragments that retain the biological activity of the native protein and hence affect plant development, developmental pathways, stress responses, metabolism, defense responses, and/or disease resistance by retaining one or more types of activity associated with the genes of the Pyk20 gene family. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a Pyk20 nucleotide sequence that encodes a biologically active portion of a Pyk20 protein of the invention will encode at least 12, 25, 30, 50, 75, 100, 125, 150, 175, 200, 225, 250, 275, 300, 325, 350, 375, 400, 425, 450, 475, 500, 525, 550, 575, 600, 625, 650, 675, or 680 contiguous amino acids, or up to the total number of amino acids present in a full-length Pyk20 protein of the invention (for example, 697 amino acids for SEQ ID NO:2).

Fragments of a Pyk20 nucleotide sequence that are useful as hybridization probes or PCR primers generally need not encode a biologically active portion of a Pyk20 protein. Thus, a fragment of a Pyk20 nucleotide sequence may encode a biologically active portion of a Pyk20 protein, or it may be a fragment that can be used as a hybridization probe or PCR primer using methods disclosed below. A biologically active portion of a Pyk20 protein can be prepared by isolating a portion of the Pyk20 nucleotide sequence of the invention, expressing the encoded portion of the Pyk20 protein (e.g., by recombinant expression in vitro), and assessing the activity of the encoded portion of the Pyk20 protein. Nucleic acid molecules that are fragments of a Pyk20 nucleotide sequence comprise at least 16, 20, 25, 30, 40, 50, 60, 70, 80, 90, 100, 125, 150, 175, 200, 225, 250, 300, 350, 400, 450, 500, 550, 600, 650, 700, 750, 800, 850, 900, 950, 1000, 1050, 1100, 1200, 1300, 1400, 1500, 1600, 1700, 1800, 1900, 2000, 2100, 2200, 2300, or 2400 nucleotides, or up to the number of nucleotides present in a full-length Pyk20 nucleotide sequence disclosed herein (for example, 2094 nucleotides for SEQ ID NO: 1).

By "variants" substantially similar sequences are intended. For nucleotide sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, such as, for example, polymerase chain reaction (PCR) and hybridization techniques as outlined below. Variant nucleotide sequences also include synthetically-derived nucleotide sequences, such as those generated, for example, by using site-directed mutagenesis but which still encode a Pyk20 protein of the invention. Generally, variants of a particular nucleotide sequence of the invention will have at least 40%, 50%, 60%, 70%, generally at least 75%, 80%, 85%, or about 90%, 91%, 92%, 93%, 94%, 95%, 96%, 97%, 98%, 99%, or more sequence identity to that particular nucleotide sequence as determined by sequence alignment programs described elsewhere herein using default parameters.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they continue to possess the desired biological activity of the native protein, hence they will continue to possess at least one activity possessed by the native Pyk20 protein. Such variants may result from, for example, genetic polymorphism or from human manipulation. Biologically active variants of a Pyk20 native protein of the invention will have at least 40%, 50%, 60%, 70%, generally at least 75%, 80%, 85%, 86%, 87%, 88%, 89%, about 90%, 91%, 92%, 93%, 94%, 95%, 96%, 97%, 98%, 99%, or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the Pyk20 proteins can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be made.

Thus, the genes and nucleotide sequences of the invention include both naturally-occurring sequences as well as mutant forms. Likewise, the proteins of the invention encompass both naturally-occurring proteins as well as variations and modified forms thereof. Such variants will continue to possess the desired characteristics of genes of the Pyk20 family described elsewhere herein. It is recognized that variants need not retain all of the activities and/or properties of the native Pyk20 protein. Obviously, the mutations that will be made in the DNA encoding the variant must not place the sequence out of reading frame and in some embodiments will not create complementary regions that could produce secondary mRNA structure. See, EP Patent Application Publication No. 75,444.

One of skill in the art can predict those deletions, insertions, and substitutions of the protein sequences encompassed herein which are not expected to produce radical changes in the characteristics of the protein. However, when it is difficult to predict the exact effect of the substitution, deletion, or insertion in advance of doing so, one skilled in the art will appreciate that the effect can be evaluated by routine screening assays. That is, the activity of Pyk20 polypeptides can be evaluated by either an enhanced response to nematode attack or a modulation in a plant developmental pathway, metabolic process, or defense or stress response when expression of the protein or polypeptide sequence is altered. For example, changes in Pyk20 gene activity may be evaluated as a change in gene transcription in genes downstream from Pyk20 in the nematode-response pathway in the plant.

Variant nucleotide sequences and proteins also encompass sequences and proteins derived from a mutagenic and recombinogenic procedure such as DNA shuffling. With such a procedure, one or more different Pyk20 coding sequences can be manipulated to create a new Pyk20 possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the Pyk20 gene of the invention and other known Pyk20 genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The polynucleotides of the present invention can also be evaluated by comparison of the percent sequence identity shared by the polypeptides they encode. For example, isolated nucleic acids which encode a polypeptide with a given percent sequence identity to the polypeptide of SEQ ID NO: 2 are disclosed. Identity can be calculated using, for example, the BLAST, TBLASTN, CLUSTALW, or GAP algorithms under default conditions. The percentage of identity to a reference sequence is at least 50% and, rounded upwards to the nearest integer, can be expressed as an integer selected from the group of integers consisting of from 50 to 99. Thus, for example, the percentage of identity to a reference sequence can be at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%.

The compositions of the invention also include the isolated nucleic acid molecule comprising the promoter nucleotide sequence set forth in SEQ ID NO:3, which sets forth the nucleotide sequence of the soybean Pyk20 promoter.

By "promoter" a regulatory region of DNA usually comprising a TATA box capable of directing RNA polymerase II to initiate RNA synthesis at the appropriate transcription initiation site for a particular coding sequence is intended. A promoter may additionally comprise other recognition sequences generally positioned upstream or 5' to the TATA box, referred to as upstream promoter elements, which influence the transcription initiation rate.

It is recognized that having identified the nucleotide sequences for the promoter regions disclosed herein, it is within the state of the art to isolate and identify additional regulatory elements in the 5' untranslated region upstream from the particular promoter regions defined herein. Thus for example, the promoter regions disclosed herein may further comprise upstream regulatory elements that confer tissue-preferred expression of heterologous nucleotide sequences operably linked to the disclosed promoter sequence. See particularly, Australian Patent No. AU-A-77751/94 and U.S. Pat. Nos. 5,466,785 and 5,635,618. It is also recognized by those of skill in the art that regulatory elements may be found in transcribed regions of a gene, for example in the region between transcription start and translation start as well as 3' to the end of translation; such elements may be found in the sequence set forth in SEQ ID NO:5. Regulatory elements, as used herein, may also be found within the coding region itself.

Fragments and variants of the disclosed Pyk20 promoter sequences are also encompassed by the present invention. By "fragment" a portion of the nucleotide sequence is intended. Fragments of a nucleotide sequence may retain biological activity and hence retain their transcriptional regulatory activity. Thus, for example, less than the entire promoter sequence disclosed herein may be utilized to drive expression of an operably linked nucleotide sequence of interest, such as a nucleotide sequence encoding a heterologous nematode-resistance polypeptide. Alternatively, fragments of a nucleotide sequence that are useful as hybridization probes generally do not retain biological activity. Thus, a fragment of the Pyk20 promoter nucleotide sequence may encode a biologically active portion of the Pyk20 promoter, or it may be a fragment that can be used as a hybridization probe or PCR primer using methods disclosed below. A biologically active portion of a Pyk20 promoter can be prepared by isolating a portion of one of the Pyk20 promoter nucleotide sequences of the invention, and assessing the activity of the portion of the Pyk20 promoter. Nucleic acid molecules that are fragments of a Pyk20 promoter nucleotide sequence comprise at least about 16 to 20 nucleotides to about 30, 40, 50, 60, 70, 80, 90, 100, 150, 200, 250, 300, 350, 400, 450, 500, 550, 600, 650, 700, 750, 800, 850, 900, 950, 1000, 1050, 1100, 1200, 1300, 1400, 1500, 1600, 1700, 1800, 1900, or 2000 nucleotides, or up to the number of nucleotides present in a full-length Pyk20 nucleotide sequence disclosed herein (for example, 1728 nucleotides for SEQ ID NO:3).

Fragment lengths depend upon the objective to be accomplished and will also vary depending upon the particular promoter sequence. Thus, where the promoter fragment is to be used as a functional promoter, suitable promoter fragments or variants retain functional promoter activity, that is, the fragments or variants obtained are capable of impacting RNA polymerase II activity at the appropriate transcription initiation site for a particular coding sequence in response to a nematode stimulus. It is within the skill in the art to determine whether such fragments decrease expression levels or alter the nature of expression, i.e., nematode-inducible or nematode-repressible expression, and assays to determine the activity of a promoter sequence are well known in the art. For example, the production of RNA transcripts may be assayed by Northern blot hybridization. Alternatively, a Pyk20 promoter fragment or variant may be operably linked to the nucleotide sequence encoding any reporter protein, such as the β-glucuronidase protein (GUS reporter) or the luciferase protein or the like. The DNA construct may be inserted into the genome of a plant or plant cell and the mRNA or protein levels of the reporter sequence determined. See Examples 1 and 2 in the Experimental section. See also, for example, Eulgem et al., (1999) *EMBO Journal* 18: 4689–4699; U.S. Pat. No. 6,072,050, herein incorporated by reference.

By "promoter variants" promoter sequences having substantial similarity with a promoter sequence disclosed herein are intended. Generally, variants of a particular nucleotide sequence of the invention will have at least about 40%, 50%, 60%, 65%, 70%, generally at least about 75%, 80%, 85%, 86%, 87%, 88%, 89%, at least about 90%, 91%, 92%, 93%, 94%, 95%, 96%, 97%, or at least about 98%, 99% or more sequence identity to that particular nucleotide sequence as determined by sequence alignment programs described elsewhere herein using default parameters. Thus, variants may differ by only a few nucleotides, such as 50, 25, 20, 15, 10, 9, 8, 7, 6, 5, 4, 3, 2, or even 1 nucleotide. Such variants retain the nematode-regulated promoter activity of the disclosed promoter sequences. Thus variants of the Pyk20 sequence retain nematode-inducible promoter activity.

The variant promoter sequences will share substantial homology with their corresponding promoter sequence. By "substantial homology" a sequence exhibiting substantial functional and structural equivalence with the disclosed sequence is intended. Any functional or structural differences between substantially homologous sequences do not affect the ability of the sequence to function as a nematode-regulated promoter. Thus, for example, any sequence having substantial sequence homology with the sequence of a particular nematode-inducible promoter of the present invention will direct expression of an operably linked heterologous nucleotide sequence in response to a nematode stimulus. Two nucleotide sequences are considered substantially homologous when they have at least about 50%, 60%, 65%, 70%, 73%, 75%, 78%, 80%, 81%, 82%, 83%, 84%, 85%, 86%, 87%, 88%, 89%, 90%, 91%, 92%, 93%, 94%, 95%, 96%, 97%, 98% or 99% or higher sequence homology. Substantially homologous sequences of the present invention include variants of the disclosed sequences such as those that result from site-directed mutagenesis, as well as synthetically derived sequences.

The nucleotide sequences of the invention can be used to isolate corresponding sequences from other organisms, particularly other plants, more particularly other crop plants. In this manner, methods such as PCR, hybridization, and the like can be used to identify such sequences based on their sequence homology to the sequences set forth herein. Sequences isolated based on their sequence identity to the entire disease resistant sequences set forth herein or to fragments thereof are encompassed by the present invention. Such sequences include sequences that are orthologs of the disclosed sequences. By "orthologs" genes derived from a common ancestral gene and which are found in different species as a result of speciation are intended. Genes found in different species are considered orthologs when their nucleotide sequences and/or their encoded protein sequences share substantial identity as defined elsewhere herein. Functions of orthologs are often highly conserved among species. Thus, isolated sequences that have Pyk20 promoter activity or encode a Pyk20 protein and which hybridize under stringent conditions to the Pyk20 sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook. (1989) *Molecular Cloning: A Laboratory Manual* (2d ed., Cold Spring Harbor Laboratory Press, Plainview, N.Y.) (hereinafter Sambrook). See also Innis et al., eds., (1990) *PCR Protocols: A Guide to Methods and Applications* (Academic Press, New York); Innis and Gelfand, eds., (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the disease-resistant sequences of the invention. Methods for preparation of probes for hybridization and for construction of cDNA and genomic libraries are generally known in the art and are disclosed in Sambrook supra.

For example, an entire sequence disclosed herein, or one or more portions thereof, may be used as a probe capable of specifically hybridizing to corresponding nematode-response sequences, including promoters and messenger RNAs. To achieve specific hybridization under a variety of conditions, such probes include sequences that are unique among nematode-response sequences and may be at least about 10 or 15 or 17 nucleotides in length or at least about 20 or 22 or 25 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies). See, for example, Sambrook supra.

Hybridization of such sequences may be carried out under stringent conditions. By "stringent conditions" or "stringent hybridization conditions" conditions under which a probe will hybridize to its target sequence to a detectably greater degree than to other sequences (e.g., at least 2-fold over background) are intended. Stringent conditions are sequence-dependent and will be different under different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length or less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3. Incubation should be at a temperature of least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl, 0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for 30 minutes. Optionally, wash buffers may comprise about 0.1% to about 1% SDS. Duration of hybridization is generally less than about 24 hours, usually about 4 to about 12 hours.

Specificity is typically a function of post-hybridization washes, the critical factors being the ionic strength and temperature of the final wash solution. The $T_m$ (thermal melting point) is the temperature (under defined ionic strength and pH) at which 50% of a complementary target sequence hybridizes to a perfectly matched probe. For DNA—DNA hybrids, the $T_m$ can be approximated from the equation of Meinkoth and Wahl (1984) *Anal. Biochem.* 138:267–284: $T_m$=81.5° C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$.

Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), the SSC concentration may be increased so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds., (1995) *Current Protocols in Molecular Biology*, Chapter 2 (Greene Publishing and Wiley-Interscience, New York). See also, Sambrook supra.

In general, sequences that have promoter activity or encode a Pyk20 protein and which hybridize to the Pyk20 sequences disclosed herein will be at least about 40% homologous, about 50% or 60% homologous, about 70% homologous, and even about 80%, 85%, 90%, 91%, 92%, 93%, 94%, 95%, 96%, 97%, 98%, 99% or more homologous with the disclosed sequences. That is, the sequence identity of the sequences may be from about 40% to 50% identical, about 60% to 70% or 75% identical, and even about 80%, 85%, 87%, 90%, 91%, 92%, 93%, 94%, 95%, 96%, 97%, 98%, or 99% identical, or higher, so that the sequences may differ by only 10, 9, 8, 7, 6, 5, 4, 3, 2, or 1 amino acid residue or by 20, 19, 18, 17, 16, 15, 14, 13, 12, 11, 10, 9, 8, 7, 6, 5, 4, 3, 2, or 1 nucleic acid.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et a. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; and the algorithm of Karlin and Altschul (1990) *Proc. Natl. Acad. Sci. USA* 872264, and as modified in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the SeqWeb® set of GCG® programs (Accelrys, Inc., San Diego, Calif.). Alignments using these programs can be performed using the default parameters. The CLUSTAL program is described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al. (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used (see information on the world wide web by using the prefix "www." ahead of ncbi.nlm.nih.gov). Alignment may also be performed manually by inspection.

Unless otherwise stated, sequence identity/similarity values provided herein refer to the value obtained using GAP version 10 using the following parameters: % identity using a GAP Weight of 50 and a Length Weight of 3; % similarity using a Gap Weight of 12 and a Length Weight of 4, or any equivalent program. By "equivalent program" any sequence comparison program that, for any two sequences in question, generates an alignment having identical nucleotide or amino acid residue matches and an identical percent sequence identity when compared to the corresponding alignment generated by GAP Version 10 is intended.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 2 of SeqWeb® from GCG® programs (Accelrys, Inc., San Diego, Calif.). for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 2 of SeqWeb® from GCG® programs (Accelrys, Inc., San Diego, Calif.) is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 80%, 85%, 90%, 95%, or higher sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 50%, 55%, 60%, 65%, 70%, 75%, 80%, 85%, 90%, or at least 95% or higher sequence identity.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross-reactive with the polypeptide encoded by the second nucleic acid.

(e)(ii) The term "substantial identity" in the context of a peptide indicates that a peptide comprises a sequence with at least 70%, 75%, 80%, 83%, 85%, 88%, 90%, 93%, 95%, 96%, 97%, 98%, or 99% or higher sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

Compositions and methods for improving resistance to nematodes are provided. The anti-nematode compositions comprise Pyk20 promoters, as well as, genes and proteins. Particularly, the soybean Pyk20 promoter, genes and proteins are provided, as well as the *Arabidopsis* Pyk20 promoter. Because resistance to nematodes involves the plant defense response, increased resistance to nematodes may well confer increased resistance to other plant pathogens and diseases. For example, it is recognized that expression driven by pathogen-responsive promoter regions can be influenced by more than one pathogen or pest (see, for example, Strittmatter et al. (1996) *Mol. Plant Microb. Interact* 9: 68–73). Thus, in other embodiments of the invention, the nematode-regulated Pyk20 promoters can be used to create or enhance resistance of a plant to other pathogens or pests in accordance with the methods of the invention whenever infection by those pathogens or pests triggers enhanced or selective transcription from these promoters. Accordingly, the compositions and methods are useful in protecting plants against a broader spectrum of diseases and stress, including stress caused by the attack or infection of fungal pathogens, viruses, insects and the like. In some embodiments, the attack or infection induces transcription from the Pyk20 promoter at the site of infection of the plant. In this manner, a nematode-regulated Pyk20 promoter, or variant or fragment thereof, can be operably linked to a nucleotide sequence that encodes pathogen-resistance sequences.

By "resistance" in the context of pathogen-resistance, disease-resistance, or nematode resistance it is intended that the impact on the plant of the particular pathogen, disease, and/or nematode is diminished or entirely avoided. That is, in a plant showing resistance, pathogens are prevented from causing plant diseases and the associated disease symptoms, or alternatively, some or all of the disease symptoms caused by the pathogen are minimized or lessened. Genes encoding disease resistance traits include, generally, detoxification genes, such as fumonisin detoxification (U.S. Pat. No. 5,792,931); avirulence (avr) and disease resistance (R) genes (Jones et al. (1994) *Science* 266:789; Martin et al. (1993) *Science* 262:1432; Mindrinos et al. (1994) *Cell* 78:1089); and the like. In some embodiments, the expression of a Pyk20 gene product, which is either driven by a Pyk20 promoter or a heterologous promoter may be induced in response to attack or infection and confers disease resistance; i.e., production of the Pyk20 gene product which, lessens the symptoms that would ordinarily result in a plant.

The nucleic acid molecules of the present invention are useful in methods directed at creating or enhancing pathogen-resistance, more particularly nematode resistance in a plant. Improved pathogen-resistance may be accomplished by stably transforming a plant of interest with a nucleic acid molecule that comprises a nematode-regulated promoter identified herein operably linked to a pathogen-resistance sequence to produce antipathogenic activity in such plants, or by the use of such transformed plants or other products to produce antipathogenic compositions. By "antipathogenic compositions" it is intended that the compositions of the invention have antipathogenic activity and thus are capable of suppressing, controlling, and/or killing the invading pathogenic organism or pest. An antipathogenic or nematicidal composition of the invention will reduce the disease symptoms resulting from pathogen or nematode challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens and nematodes. In some embodiments, the pathogen-resistance sequence is a nematode-resistance sequence that, when expressed, produces a product that has antipathogenic properties for nematodes, and the nematode-regulated promoter is the nematode-inducible soybean Pyk20 promoter (SEQ ID NO:3).

Assays that measure antipathogenic activity are commonly known in the art, as are methods to quantitate disease resistance in plants following pathogen infection. See, for example, U.S. Pat. No. 5,614,395, herein incorporated by reference. These assays may be used to measure the activity of the promoters of the invention as well as the activity of the polypeptides of the invention. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107–15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888–1892, herein incorporated by reference). Additionally, microspectrophotometrical analysis can be used to measure the in vitro antipathogenic properties of a composition (Hu et al. (1997) *Plant Mol. Biol.* 34:949–959 and Cammue et al. (1992) *J. Biol. Chem.* 267: 2228–2233, both of which are herein incorporated by reference).

Also contemplated are antipathogenic assays directed at nematodes. Such assays are known to the skilled artisan, and may include assays directed at specific characteristics of nematode infections, such as assays directed at nematode feeding site formation. Such assays include those disclosed in U.S. Pat. Nos. 6,008,436 and 6,252,138, herein incorporated by reference.

The nematodes considered in this disclosure include parasitic nematodes such as root-knot, cyst, and lesion nematodes, including, but not limited to, *Heterodera* and *Globodera* spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode). Nematodes affecting rice include, but are not limited to, Crimp nematode, *Aphelenchoides besseyi*; Root-knot, *Meloidogyne* spp.; Rice Root nematode, *Hirschmaniella oryzae*; and Rice Stem nematode, and *Ditylenchus angustus*.

Methods for increasing pathogen resistance in a plant are provided. In some embodiments, the methods involve stably transforming a plant with a DNA construct comprising an anti-pathogenic nucleotide sequence of the invention operably linked to a promoter that drives expression in a plant. While the choice of promoter will depend on the desired timing and location of expression of the anti-pathogenic or other nucleotide sequences, desirable promoters include constitutive and pathogen-inducible promoters. In some embodiments, such a promoter will be a Pyk20 promoter of the invention, as further discussed below. These methods may find use in agriculture, particularly in limiting the impact of plant pathogens or pests on crop plants. Thus, transformed plants, plant cells, plant tissues and seeds thereof are provided by the present invention.

Additionally, the compositions of the invention can be used in formulations for their disease resistance activities. The proteins of the invention can be formulated with an acceptable carrier into a pesticidal or nematicidal composition(s) that is, for example: a suspension, a solution, an emulsion, a dusting powder, a dispersible granule, a wettable powder, an emulsifiable concentrate, an aerosol, an impregnated granule, an adjuvant, a coatable paste, or an encapsulation in, for example, polymer substances.

It is understood in the art that plant DNA viruses and fungal pathogens remodel the control of the host replication and gene expression machinery to accomplish their own replication and effective infection. The plant response to stress, such as stress caused by nematode attack, is known to involve many basic biochemical pathways and cellular functions. Hence, the sequences of the invention find use in altering the defense mechanisms of a host plant to provide broad-based resistance to diseases or pests. Additionally, the present invention may be useful in preventing corruption of the cell machinery by viruses and other plant pathogens.

The compositions and methods of the invention function to inhibit or prevent plant diseases by suppressing, controlling, and/or killing the invading pathogenic organism. Further, the promoters of the invention may provide control of gene expression that may be helpful in avoiding or ameliorating disease symptoms. It is recognized that the present invention is not dependent upon a particular mechanism of defense. Rather, the compositions and methods of the invention work to increase resistance of the plant to pathogens independent of how that resistance is increased or achieved.

The methods of the invention can be used with other methods available in the art for enhancing disease resistance in plants. Similarly, in addition to being used singly, the pathogen-resistance sequences, more particularly the nematode-resistance sequences, described herein may be used in combination with sequences encoding other proteins or agents to protect against plant diseases and pathogens. Other plant defense proteins include those described in U.S. Pat. No. 6,476,292 and U.S. patent application Ser. No. 09/256,158, now abandoned, both of which are herein incorporated by reference.

The present invention may be used in conjunction with one or more other methods to increase disease resistance. In some embodiments of the invention, a second nucleotide sequence is transformed into a plant to increase the plant's resistance to pathogens or pests. In these embodiments, any one of a variety of second nucleotide sequences may be utilized. It is recognized that such second nucleotide sequences may be used in either the sense or antisense orientation.

In other embodiments, the methods of the present invention involve stably transforming a plant with a DNA construct comprising a promoter of the invention linked to a nucleotide sequence which confers increased resistance to pathogens or pests. In this manner, the Pyk20 promoters disclosed herein may provide regulation of expression of operably linked coding regions to control pathogen and pests. Additionally, the Pyk20 promoters disclosed herein are useful for genetic engineering of plants to express a phenotype of interest. The promoter sequences may be used to drive expression of any heterologous nucleotide sequence. Alternatively, the Pyk20 promoter sequence may be used to drive expression of its native, i.e., naturally occurring, Pyk20 gene sequence disclosed herein. In such an embodiment, the phenotype of the plant is altered. In some embodiments, the Pyk20 promoter sequences are operably linked to a nematicidal nucleotide sequence and drive expression of said sequence in a plant cell. The Pyk20 promoter sequences may therefore be used in creating or enhancing pathogen, disease, or pest resistance in a transformed plant.

In some embodiments, the nucleic acid molecules comprising Pyk20 sequences of the invention are provided in expression cassettes or DNA constructs for expression in the plant of interest. Such cassettes will include 5' and 3' regulatory sequences operably linked to a Pyk20 sequence of the invention. The cassette may additionally contain at least one additional gene to be cotransformed into the organism. Alternatively, the additional gene(s) can be provided on multiple expression cassettes.

Such an expression cassette is provided with a plurality of restriction sites for insertion of the Pyk20 sequence to be under the transcriptional regulation of the regulatory regions. The expression cassette may additionally contain selectable marker genes.

The expression cassette will include in the 5'-3' direction of transcription, a transcriptional and translational initiation region, a Pyk20 DNA sequence of the invention, and a transcriptional and translational termination region functional in plants. The transcriptional initiation region, or promoter, may be native or analogous or foreign or heterologous to the plant host. Additionally, the promoter may be the natural sequence or alternatively a synthetic sequence. By "foreign" it is intended that the transcriptional initiation region is not found in the native plant into which the transcriptional initiation region is introduced. As used herein, a "chimeric gene" comprises a coding sequence operably linked to a transcription initiation region that is heterologous to the coding sequence.

While it may be preferable to express the Pyk20 sequences using heterologous promoters, the native promoter sequences may be used. Such constructs would change expression levels of the Pyk20 protein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to enhance expression in a given host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include, but are not limited to: picornavirus leaders, for example, EMCV leader (Encephalomyocarditis 5' noncoding region) (Elroy-Stein et al. (1989) *Proc. Nat'l. Acad. Sci. USA* 86:6126–6130); potyvirus leaders, for example, TEV leader (Tobacco Etch Virus) (Allison et al. (1986) *Virology* 154:9–20); MDMV leader (Maize Dwarf Mosaic Virus); human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed., Cech (Liss, New York), pp. 237–256); and maize chlorotic mottle virus leader (MCMV) (Lommel et al. (1991). *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells.

Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate, bromoxynil, imidazolinones, and 2,4-dichlorophenoxyacetate (2,4-D). See generally, Yarranton (1992) *Curr. Opin. Biotech.* 3:506–511; Christopherson et al. (1992) *Proc. Natl. Acad. Sci. USA* 89:6314–6318; Yao et al. (1992) *Cell* 71:63–72; Reznikoff (1992) *Mol. Microbiol.* 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol.* 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res.* 19:4647–4653; Hillenand-Wissman (1989) *Topics Mol. Struc. Biol.* 10:143–162; Degenkolb et al. (1991) *Antimicrob. Agents Chemother.* 35:1591–1595; Kleinschnidt et al. (1988) *Biochemistry* 27:1094–1104; Bonin (1993) Ph.D. Thesis, University of Heidelberg; Gossen et al. (1992) *Proc. Natl. Acad. Sci. USA* 89:5547–5551; Oliva et al. (1992) *Antimicrob. Agents Chemother.* 36:913–919; Hlavka et al. (1985) *Handbook of Experimental Pharmacology*, Vol. 78 (Springer-Verlag, Berlin); Gill et al. (1988) *Nature* 334: 721–724 and U.S. patent application Ser. No. 10/072,307. Such disclosures are herein incorporated by reference.

The above list of selectable marker genes is not meant to be limiting. Any selectable marker gene can be used in the present invention. Alternatively, nematode-resistance may be directly selected by inoculating nematodes into the transformed protoplasts, cells, or tissues. Both methods of selection are generally known in the art.

A number of promoters can be used in the practice of the invention. The promoters can be selected based on the desired outcome. That is, the nucleic acids can be combined with constitutive, tissue-preferred, or other promoters for expression in plants.

Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol.* 12:619–632 and Christensen et al. (1992) *Plant Mol. Biol.* 18:675–689); pEMU (Last et al. (1991) *Theor. Appl. Genet.* 81:581–588); MAS (Velten et al. (1984) *EMBO J.* 3:2723–2730); ALS promoter (U.S. Pat. No. 5,659,026), and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245–254; Uknes et al. (1992) *Plant Cell* 4:645–656; and Van Loon (1985) *Plant Mol. Virol.* 4:111–116. See also, WO 99/43819, herein incorporated by reference.

Of interest are promoters that are expressed locally at or near the site of pathogen infection or pest or insect damage. See, for example, Marineau et al. (1987) *Plant Mol. Biol.* 9:335–342; Matton et al. (1989) *Molecular Plant-Microbe Interactions* 2:325–331; Somssich et al. (1986) *Proc. Natl. Acad. Sci. USA* 83:2427–2430; Somssich et al. (1988) *Mol. Gen. Genet* 2:93–98; and Yang (1996) *Proc. Natl. Acad. Sci. USA* 93:14972–14977. See also, Chen et al. (1996) *Plant J.* 10:955–966; Zhang et al. (1994) *Proc. Natl. Acad. Sci. USA* 91:2507–2511; Warner et al. (1993) *Plant J.* 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, the expression of which is induced by the pathogen *Fusarium moniliforme* (see, for example, Cordero et al. (1992) *Physiol. Mol. Plant Path.* 41:189–200).

Additionally, as pathogens find entry into plants through wounds or insect damage, a wound-inducible promoter may be used in the constructions of the invention. Such wound-inducible promoters include the potato proteinase inhibitor (pin II) gene (Ryan (1990) *Ann. Rev. Phytopath.* 28:425–449; Duan et al. (1996) *Nature Biotechnology* 14:494–498); wun1 and wun2, U.S. Pat. No. 5,428,148; win1 and win2 (Stanford et al. (1989) *Mol. Gen. Genet.* 215:200–208); systemin (McGurl et al. (1992) *Science* 225: 1570–1573); WIP1 (Rohmeier et al. (1993) *Plant Mol. Biol.* 22:783–792 and Eckelkamp et al. (1993) *FEBS Letters* 323:73–76); MPI gene (Corderok et al. (1994) *Plant J.* 6(2):141–150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to: the maize In2-2 promoter, which is activated by benzenesulfonamide herbicide safeners; the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters. See, for example, the glucocorticoid-inducible promoter in Schena et al. (1991) *Proc. Natl. Acad. Sci. USA* 88:10421–10425 and McNellis et al. (1998) *Plant J.* 14(2):247–257 and the tetracycline-inducible and tetracycline-repressible promoters for example, Gatz et al. (1991) *Mol. Gen. Genet.* 227:229–237, and U.S. Pat. Nos. 5,814,618 and 5,789,156, herein incorporated by reference.

Tissue-preferred promoters can be utilized to target enhanced Pyk20 expression within a particular plant tissue. Tissue-preferred promoters include those disclosed in Yamamoto et al. (1997) *Plant J.* 12(2):255–265; Kawamata et al. (1997) *Plant Cell Physiol.* 38(7):792–803; Hansen et al. (1997) *Mol. Gen Genet.* 254(3):337–343; Russell et al. (1997) *Transgenic Res.* 6(2):157–168; Rinehart et al. (1996) *Plant Physiol.* 112(3):1331–1341; Van Camp et al. (1996) *Plant Physiol.* 112(2):525–535; Canevascini et al. (1996) *Plant Physiol.* 112(2):513–524; Yamamoto et al. (1994) *Plant Cell Physiol.* 35(5):773–778; Lam (1994) *Results Probl. Cell Differ.* 20:181–196; Orozco et al. (1993) *Plant*

Mol. Biol. 23(6):1129–1138; Matsuoka et al. (1993) Proc Natl. Acad. Sci. USA 90(20):9586–9590; and Guevara-Garcia et al. (1993) Plant J. 4(3):495–505. Such promoters can be modified, if necessary, for weak expression.

Leaf-specific promoters are known in the art. See, for example, Yamamoto et al. (1997) Plant J. 12(2):255–265; Kwon et al. (1994) Plant Physiol. 105:357–67; Yamamoto et al. (1994) Plant Cell Physiol. 35(5):773–778; Gotor et al. (1993) Plant J. 3:509–18; Orozco et al. (1993) Plant Mol. Biol. 23(6):1129–1138; and Matsuoka et al. (1993) Proc. Natl. Acad. Sci. USA 90(20):9586–9590.

Root-preferred promoters are known and can be selected from the many available from the literature or isolated de novo from various compatible species. See, for example, Hire et al. (1992) Plant Mol. Biol. 20(2):207–218 (soybean root-specific glutamine synthetase gene); Keller et al. (1991) Plant Cell 3(10):1051–1061 (root-specific control element in the GRP 1.8 gene of French bean); Sanger et al. (1990) Plant Mol. Biol. 14(3):433–443 (root-specific promoter of the mannopine synthase (MAS) gene of Agrobacterium tumefaciens); and Miao et al. (1991) Plant Cell 3(1):11–22 (full-length cDNA clone encoding cytosolic glutamine synthetase (GS), which is expressed in roots and root nodules of soybean). See also Bogusz et al. (1990) Plant Cell 2(7): 633–641, which discloses two root-specific promoters isolated from hemoglobin genes from the nitrogen-fixing non-legume Parasponia andersonii and the related non-nitrogen-fixing nonlegume Trema tomentosa. The promoters of these genes were linked to a β-glucuronidase reporter gene and introduced into both the nonlegume Nicotiana tabacum and the legume Lotus corniculatus, and in both instances root-specific promoter activity was preserved. Leach et al. (1991) describe their analysis of the promoters of the highly expressed roIC and roID root-inducing genes of Agrobacterium rhizogenes (see Plant Science (Limerick) 79(1): 69–76). They concluded that enhancer and tissue-preferred DNA determinants are dissociated in those promoters. Teeri et al. (1989) EMBO J. 8(2):343–350 used gene fusion to lacZ to show that the Agrobacterium T-DNA gene encoding octopine synthase is especially active in the epidermis of the root tip and that the TR2' gene is root specific in the intact plant and stimulated by wounding in leaf tissue, which is an especially desirable combination of characteristics for use with an insecticidal or larvicidal gene. The TR1' gene, fused to nptII (neomycin phosphotransferase II), showed similar characteristics. Additional root-preferred promoters include the VfENOD-GRP3 gene promoter (Kuster et al. (1995) Plant Mol. Biol. 29(4):759–772); the ZRP2 promoter (U.S. Pat. No. 5,633,636); the IFS1 promoter (U.S. patent application Ser. No. 10/104,706) and the roIB promoter (Capana et al. (1994) Plant Mol. Biol. 25(4):681–691). See also U.S. Pat. Nos. 5,837,876; 5,750,386; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) BioEssays 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and celA (cellulose synthase) (see U.S. Pat. No. 6,225,529, herein incorporated by reference). Gamma-zein is an endosperm-specific promoter. Glob-1 is an embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, which discloses seed-preferred promoters from end1 and end2 genes; herein incorporated by reference.

Where low level expression is desired, weak promoters will be used. Generally, by "weak promoter" a promoter that drives expression of a coding sequence at a low level is intended. By "low level" levels of about 1/1000 transcripts to about 1/100,000 transcripts to about 1/500,000 transcripts per cell are intended. Alternatively, it is recognized that weak promoters also include promoters that are expressed in only a few cells and not in others to give a total low level of expression. Where a promoter is expressed at unacceptably high levels, portions of the promoter sequence can be deleted or modified to decrease expression levels.

As used herein, "vector" refers to a molecule such as a plasmid, cosmid or bacterial phage for introducing a nucleotide construct and/or expression cassette into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

The methods of the invention involve introducing a nucleotide construct into a plant. By "introducing" presenting to the plant the nucleotide construct in such a manner that the construct gains access to the interior of a cell of the plant is intended. The methods of the invention do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated transformation methods.

By "stable transformation" it is intended that the nucleotide construct introduced into a plant integrates into the genome of the plant and is capable of being inherited by progeny thereof. By "transient transformation" it is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that the Pyk20 protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931, herein incorporated by reference.

A variety of other transformation protocols are contemplated in the present invention. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606), *Agrobacterium*-mediated transformation (U.S. Pat. Nos. 5,563,055 and 5,981,840), direct gene transfer (Paszkowski et al. (1984) *EMBO J.* 3:2717–2722), and ballistic particle acceleration (see, for example, U.S. Pat. Nos. 4,945,050; 5,879,918; 5,886,244; 5,932,782; Tomes et al. (1995) *Plant Cell, Tissue, and Organ Culture: Fundamental Methods*, eds., Gamborg and Phillips (Springer-Verlag, Berlin); McCabe et al. (1988) *Biotechnology* 6:923–926); and Lec1 transformation (WO 00/28058). See also, Weissinger et al. (1988) *Ann. Rev. Genet* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); U.S. Pat. Nos. 5,240,855; 5,322,783 and 5,324,646; Klein et al. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, eds., Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobactenum tumefaciens*); all of which are herein incorporated by reference. Sunflower meristem tissue transformation can be performed as outlined in the following: EP 0486233, Malone-Schoneberg et al. (1994) *Plant Science* 103:199–207, Schrammeijer et al. (1990) *Plant Cell Rep.* 9: 55–60; Bidney et al. (1992) *Plant Mol. Biol.* 18: 301–313, Holsters et al. (1978) *Mol. Gen. Genet* 163:181–187; all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrids having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, monocots and dicots. Examples of plant species of interest include, but are not limited to, corn (*Zea mays*), *Brassica* spp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulchenima*), and chrysanthemum.

Preferred plants of the present invention may be crop plants (for example, alfalfa, sunflower, *Brassica*, cotton, safflower, peanut, sorghum, wheat, millet, tobacco, etc.), corn or soybean plants.

Plants of particular interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mung bean, lima bean, fava bean, lentils, chickpea, etc.

Other plants of interest that are susceptible to diseases caused by nematodes, and the corresponding nematodes of interest include, but are not limited to, those presented in Table 1:

TABLE 1

Nematode species and the plants they affect

| Nematode species | Plants affected |
|---|---|
| *Anguina tritici* | Cereals (emmer, rye, spelt wheat), |
| *Aphelenchiodes besseyi* | Rice |
| *Aphelenchiodes* spp. | Strawberry |
| *Belonolaimus* spp. | Beans & peas, citrus, cotton, peanut soybean, sugar cane |
| *Bidera avenae* | Cereals (oat, wheat) |
| *Cacopaurus pestis* | Walnut |
| *Criconemella* spp. | Peanut, pineapple, peach |
| *Ditylenchus* spp. | Alfalfa, cereals (rye, oat), sugar beet, tobacco, grasses, potato, rice |
| *Globodera* spp. *pallida* | Potato, tobacco |
| *Helicotylenchus* spp. | Banana, beans & peas, coffee, pineapple, sugar cane, tea |
| *Hemicriconemoides kanayaensis* | Tea |
| *Hemicycliophora arenaria* | Citrus |

TABLE 1-continued

Nematode species and the plants they affect

| Nematode species | Plants affected |
|---|---|
| *Heterodera* spp | Beans & peas, chickpeas, pigeon pea, soybean, rice, sugar cane, sugar beet, clover |
| *Hirchmanniella* spp. | Rice |
| *Hoplolaimus* spp. | Corn, soybean, cotton, chickpea, pigeon pea, sugar cane |
| *Longidorus* spp | Corn, grasses, small fruits, sugar beet, sugar cane, cherry |
| *Meloidogyne* spp. | Alfalfa, banana, beans & peas, cassava, cereals, chickpea, citrus, clover, coffee, cotton, grapes, peanut, pigeon pea, pineapple, potato, rice, small fruits, soybean, sugar beet, sugar cane, tea, tobacco, tomato, tree fruits |
| *Nacobbus aberrans* | Potato, sugar beet |
| *Paratrichodorus* spp. | Beans & peas, grasses, pineapple, small fruits, citrus, corn, cotton, potato, sugar beet, sugar cane, tobacco |
| *Paratylenchus* spp | Alfalfa, cereals (wheat), pineapple, tree fruits, tea, coffee |
| *Pratylenchus* spp | Alfalfa, banana, coffee, cereals (oat, wheat, barley, rye), chickpea, citrus, corn, cotton, grasses, peanut, pigeon pea, pineapple, potato, small fruits, sugar cane, tea, tobacco, tomato, tree fruits, grapes |
| *Radopholus* spp. | Sugar cane, citrus, banana, citrus, coffee, tea |
| *Rhadinaphelenchus cocophilus* | Coconut |
| *Rotylenchulus reniformis* | Banana, beans & peas, cassava, chickpea, coffee, cotton, grapes, pigeon pea, pineapple |
| *Scutellonema* spp | Sugar cane |
| *Subanguina radicicola* | Cereals (oat, barley, wheat, rye) |
| *Trichodorus* spp. | Beans & peas, citrus, sugar beet, tobacco, potato |
| *Tylenchorhynchus* spp. | Cereals (wheat, oat), cotton, sugar cane, tobacco |
| *Tylenchulus* spp. | Olive, citrus, grapes |
| *Xiphinema* spp | Alfalfa, citrus, grapes, grasses, small fruits, sugar cane, tree fruits, tobacco |

It is recognized that antisense constructions complementary to at least a portion of the messenger RNA (mRNA) for the Pyk20 sequences of the present invention can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, 85%, 90%, 95% or more sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, such as greater than about 65%, 75%, 85%, 95%, or higher sequence identity. See, U.S. Pat. Nos. 5,283,184 and 5,034,323; herein incorporated by reference. Posttranscriptional gene silencing may also result from the presence of RNA or double-stranded RNA which is thought to trigger cell-mediated degradation of homologous RNAs. See, for example, Matzke et al., (2001) *Curr. Op. Genet. Dev.* 11:221–227.

The nucleotide sequences of the Pyk20 promoters disclosed in the present invention, as well as variants and fragments thereof, are useful in the genetic manipulation of any plant when assembled with a construct such that the promoter sequence is operably linked to a nucleotide sequence encoding a heterologous protein of interest. In this manner, the nucleotide sequences of the Pyk20 promoter of the invention can be provided in expression cassettes along with heterologous nucleotide sequences for expression in the plant of interest. Such an expression cassette is provided with a plurality of restriction sites for insertion of the nucleotide sequence to be under the transcriptional regulation of the nematode-regulated promoter region. The expression cassette may additionally contain selectable marker genes.

The expression cassette will include in the 5'-to-3' direction of transcription a transcriptional and translational initiation region comprising the nematode-regulated Pyk20 promoter (or variant or fragment thereof, a nucleotide sequence of interest which may be a heterologous nucleotide sequence or a Pyk20 sequence, and a transcriptional and translational termination region functional in plants. The termination region may be native with the transcriptional initiation region comprising one of the promoter nucleotide sequences of the present invention, may be native with the DNA sequence of interest, or may be derived from another source. Convenient termination regions are available from the Ti-plasmid of *A. tumefaciens*, such as the octopine synthase and nopaline synthase termination regions (see references cited herein above). An expression cassette comprising a Pyk20 promoter sequence may also contain features or modifications as described herein above for expression cassettes comprising nucleotide sequences of a Pyk20 coding region of the invention.

The expression cassette comprising the Pyk20 promoter sequence (or variant or fragment thereof) operably linked to a heterologous nucleotide sequence of interest may also contain at least one additional nucleotide sequence for a gene to be cotransformed into the organism. Alternatively, the additional sequence(s) can be provided on another expression cassette.

The promoter for the Pyk20 gene may regulate expression of operably linked nucleotide sequences in an inducible manner. That is, expression of the operably linked nucleotide sequences in a plant cell is induced in response to a stimulus. By "stimulus" a chemical, which may be applied externally or may accumulate in response to another external stimulus; other stresses such as environmental stresses, including but not limited to drought, temperature, and salinity; or other factor such as a pathogen, which may, for example, induce expression as a result of invading a plant cell is intended. For example, a nematode invading a plant cell may produce a stimulus.

Synthetic promoters are known in the art. Such promoters comprise upstream promoter elements (also referred to as "fragments" or "subsequences") of one nucleotide sequence operably linked to at least one promoter element of another nucleotide sequence. Thus, a "synthetic" promoter comprises sequences that are assembled in a non-native configuration. In an embodiment of the invention, heterologous gene expression is controlled by a synthetic hybrid promoter comprising the Pyk20 promoter sequences of the invention, or a variant or fragment thereof, operably linked to upstream promoter element(s) from a heterologous promoter. Upstream promoter elements that are involved in the plant defense system have been identified and may be used to generate a synthetic promoter. See, for example, Rushton and Somssich (1998) *Curr. Opin. Plant Biol.* 1: 311–315. Also, for example, the UAR of the maize ubiquitin-1 promoter has DNA elements that up-regulate promoter activity in response to nematode stimulus (see, U.S. patent application Ser. No. 10/266,416). These elements can be as small as 4 or 6 base pairs, and can regulate nematode-responsive activity of other promoters by cloning one or more copies of the element into the promoters. Alternatively, a synthetic Pyk20 promoter sequence may comprise duplications of upstream elements found within the Pyk20 promoter sequence. In order to increase transcription levels, enhancers may be utilized in combination with the promoter regions of the invention. Enhancers are nucleotide sequences that act to increase the expression of a promoter region. Enhancers are known in the art and include the SV40 enhancer region, the 35S enhancer element, and the like.

It is recognized that the promoter sequence of the invention may be used with its native Pyk20 coding sequences. A DNA construct comprising the Pyk20 promoter operably linked with its native Pyk20 gene may be used to transform any plant of interest to bring about a desired phenotypic change, such as enhanced disease or pest resistance. Where the promoter and its native gene are naturally occurring within the plant, i.e., in soybean, transformation of the plant with these operably linked sequences also results in either a change in phenotype such as enhanced stress response or the insertion of operably linked sequences within a different region of the chromosome, thereby altering the plant's genome.

In another embodiment of the invention, expression cassettes will comprise a transcriptional initiation region comprising the Pyk20 promoter nucleotide sequences disclosed herein, or variants or fragments thereof, operably linked to the heterologous nucleotide sequence whose expression is to be controlled by the inducible promoter of the invention.

The promoter nucleotide sequences and methods disclosed herein are useful in regulating expression of any heterologous nucleotide sequence in a host plant in order to vary the phenotype of a plant. Various changes in phenotype are of interest including modifying the composition and content of root cells in response to nematode attack, and the like. These results can be achieved by providing expression of heterologous products or increased expression of endogenous products in plants. Alternatively, these results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those affecting kernel size, sucrose loading, and the like.

Agronomically important traits such as oil, starch, and protein content can be genetically altered in addition to using traditional breeding methods. The quality of grain is reflected in traits such as levels and types of oils, saturated and unsaturated, quality and quantity of essential amino acids, and levels of cellulose. Modifications include increasing the content of oleic acid, saturated and unsaturated oils, increasing levels of lysine and sulfur, providing essential amino acids, and also the modification of starch. Hordothionin protein modifications are described in U.S. Pat. Nos. 5,885,801; 5,885,802; 5,990,389; and 5,703,049; herein incorporated by reference. Another example is lysine and/or sulfur rich seed protein encoded by the soybean 2S albumin described in U.S. Pat. No. 5,850,016 and the chymotrypsin inhibitor from barley, described in Williamson et al. (1987) *Eur. J. Biochem.* 165:99–106, the disclosures of which are herein incorporated by reference.

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor (see, WO 98/20133 the disclosure of which is herein incorporated by reference). Other proteins include methionine-rich plant proteins such as from sunflower seed (Lilley et al. (1989) *Proceedings of the World Congress on Vegetable Protein Utilization in Human Foods and Animal Feedstuffs*, ed., Applewhite (American Oil Chemists Society, Champaign, Ill.), pp. 497–502; herein incorporated by reference); corn (Pedersen et al. (1986) *J. Biol. Chem.* 261:6279 and Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Insect resistance genes may encode resistance to pests that have great yield drag such as rootworm, cutworm, European Corn Borer, and the like. Such genes include, for example, *Bacillus thuringiensis* toxic protein genes (see, U.S. Pat. Nos. 5,366,892; 5,747,450; 5,736,514; 5,723,756; 5,593,881 and Geiser et al. (1986) *Gene* 48:109); lectins (Van Damme et al. (1994) *Plant Mol. Biol.* 24:825); and the like.

Genes encoding disease resistance traits include detoxification genes, such as those against fumonisin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, while the nptII gene encodes resistance to the antibiotics kanamycin and geneticin and the ALS-gene mutants encode resistance to the herbicide chlorsulfuron. Glyphosate tolerant plants are known in the art. (See, U.S. Pat. No. 5,627,061 and WO 02/36782).

Sterility genes can also be encoded in an expression cassette and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) *J. Bacteriol.* 170:5837–5847) facilitate expression of polyhyroxyalkanoates (PHAs).

Exogenous products include plant enzymes and products, as well as, those from other sources including prokaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

In those instances where it is desirable to have the expressed product of the heterologous nucleotide sequence of interest directed to a particular organelle, such as the chloroplast or mitochondrion, or secreted at the cell's surface or extracellularly, the expression cassette may further comprise a coding sequence for a transit peptide. Such transit peptides are well known in the art and include, but are not limited to, the transit peptide for the acyl carrier protein, the small subunit of RUBISCO, plant EPSP synthase, and the like.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104–126; Clark et al. (1989) *J. Biol. Chem.* 264:17544–17550; Della-Cioppa et al. (1987) *Plant Physiol.* 84:965–968; Romer et al. (1993) *Biochem. Biophys. Res. Commun.* 196:1414–1421; and Shah et al. (1986) *Science* 233:478–481.

In particular, chloroplast targeting sequences are known in the art and include the chloroplast small subunit of ribulose-1,5-bisphosphate carboxylase (Rubisco) (de Castro Silva Filho et al. (1996) *Plant Mol. Biol.* 30:769–780; Schnell et al. (1991) *J. Biol. Chem.* 266(5):3335–3342); 5-(enolpyruvyl)shikimate-3-phosphate synthase (EPSPS) (Archer et al. (1990) *J. Bioenerg. Biomemb.* 22(6):789–810); tryptophan synthase (Zhao et al. (1995) *J. Biol. Chem.* 270(11):6081–6087); plastocyanin (Lawrence et al. (1997) *J. Biol. Chem.* 272(33):20357–20363); chorismate synthase (Schmidt et al. (1993) *J. Biol. Chem.* 268 (36):27447–27457); and the light harvesting chlorophyll a/b binding protein (LHBP) (Lamppa et al. (1988) *J. Biol. Chem.* 263:14996–14999).

Methods for transformation of chloroplasts are known in the art. See, for example, Svab et al. (1990) *Proc. Natl. Acad. Sci. USA* 87:8526–8530; Svab et al. (1993) *Proc. Natl. Acad. Sci. USA* 90:913–917; and Svab et al. (1993) *EMBO J.* 12:601–606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301–7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of a mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that the methods of the present invention do not depend on the incorporation of the entire nucleotide construct into the genome. Rather, the methods of the present invention only require that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774–8778; herein incorporated by reference.

The following examples are offered by way of illustration and not by way of limitation.

EXPERIMENTAL

Example 1

Isolation and Characterization of Pyk20 Gene and Promoter

Materials and Methods

Soybean plants of cultivars Bell and YB17E were grown in the greenhouse and growth chamber. Plant materials were harvested and ground in liquid nitrogen. Total RNA was isolated from the plant material by the Tri-pure Method (Boehringer) according to the manufacturer's instructions. Genomic DNA was isolated using a DNeasy Plant mini kit (Qiagen) according to the manufacturer's instructions.

PCRs (polymerase chain reactions) were performed in a total volume of 25 µL in a solution of: 10 mM Tris-HCL, pH 8.3; 1.5 mM $MgCl_2$; 50 mM KCl; 0.1 mM dNTPs; 0.25 µM of each primer, as appropriate; and 0.5 Units of either Advantage cDNA polymerase mix (Clontech) or Pwo DNA polymerase (Boehringer).

PCR-amplified fragments were analyzed by gel electrophoresis. Fragments of the appropriate molecular weight were individually isolated from the gel and used as the substrate for a second round of PCR amplification, which was performed using the same conditions as the initial amplification. Where the second-round PCR reaction showed a single band with the expected molecular weight, that product was isolated and cloned into the TA vector (Clontech) per the manufacturer's instructions. These clones were then sequenced using standard procedures and an Applied Biosystems 373A (ABI) automated sequencer. DNA sequence analysis was carried out with the Sequencer (3.0) (Gene Codes Corporation). Multiple-sequence alignments (Clustal W) of the DNA sequence were performed using the Clustal W program (CuraGen) (Higgins and Sharp (1988) *Gene* 73: 237–244; Higgins and Sharp (1989) *CABIOS* 5: 151–53 and Thompson et al. (1994) *Nucl. Acids Res.* 22: 4673–4680). BLAST was also used for sequence analysis (Altschul et al. (1990) *J. Mol. Biol.* 215(3): 403–10).

Results

The soybean coding region which corresponds to the *Arabidopsis* Pyk20 cDNA (GenBank Accession #Y11994) was identified by a BLAST search of the DuPont®/Pioneer® EST database. This clone, soybean EST sr1.0008.a3, was obtained and sequenced. Analysis of soybean EST clone sr1.0008.a3 showed that the clone contained a full-length cDNA encoding Pyk20. The nucleotide and predicted amino acid sequence of soybean Pyk20 is set forth in SEQ ID NOs: 1 and 2, respectively. The soybean Pyk20 protein is 697 amino acids in length with a calculated molecular mass of 76 kDa and a pi at 8.96; it also has an amino-terminal signal sequence. Sequence comparison shows that the predicted amino acid sequence of soybean Pyk20 has substantial identity (46%) to the previously reported *Arabidopsis* Pyk20 (FIG. 1).

The soybean Pyk20 promoter was isolated from soybean genomic DNA using the Universal GenomeWalker Kit (Clontech) according to the manufacturer's instruction. In this procedure, restriction-digested genomic DNA was ligated with an adaptor to construct pools of genomic DNA fragments for walking by PCR. This process used an adaptor primer (Clontech) and a customized, gene-specific primer (SEQ ID NO: 6) (5'-CTCTTCCTCGTTCCCTCTCT-TCATCCTA-3'). Sequence analysis showed that the soybean Pyk20 promoter clone, 1728 nucleotides in length, contains a sequence motif (5'-TTGACC-3') known as a reverse W-box motif (Rushton et al. (1996) *EMBO J.* 15: 5690–5700 and Eulgem et al. (1999) *EMBO J.* 18(17): 4689–99). This represents the WKRY protein recognition element.

The *Arabidopsis* Pyk20 promoter was isolated using *Arabidopsis* Pyk20 cDNA ("AtPyk20"; GenBank Accession #Y11994), which was used in a BLAST search to identify a corresponding *Arabidopsis* BAC clone. This search identified a clone, T19L18, which contained the *Arabidopsis* Pyk20 coding region as well as upstream regions. The identified clone was obtained from the *Arabidopsis* Biological Resource Center. Two primers were designed to PCR-amplify and clone the *Arabidopsis* Pyk20 promoter. These primers had the following sequences: (SEQ ID NO: 7) 5'-TGCCACCGAGTATTTTGAACTCCG-3'; and (SEQ ID NO: 8) 5'-GCATCATTCACATGAAGCCGAGG-3'. Using these primers, the promoter of the *Arabidopsis* Pyk20 gene was PCR-amplified from the BAC clone; the sequence was determined and is set forth in SEQ ID NO:4. Sequence analysis showed that the *Arabidopsis* Pyk20 promoter clone, 2010 nucleotides in length, contains a reversed GCC box (Ohme-Takagi et al., (1995) *Plant Cell* 7: 173–182 and Yamamoto et al. (1999) *Plant J.* 20(5): 571–79). This GCC box has the sequence 5'-GTCGGC-3'. This promoter also contains a TATA box element. The sequence of this clone of the AtPyk20 promoter region was identical to the T19L18 BAC sequence in the *Arabidopsis* genome database (Accession No. AC004747; Lin et al. (1999) *Nature* 402: 761–68; see also, GenBank #ATH249204).

The soybean Pyk20 promoter was cloned into a binary vector in operable linkage with the GUS gene so that the SoyPyk20 promoter drove GUS expression. This binary vector, designated SoyPyk20::GUS (PHP 18280), was then used to transform soybean hairy roots using the procedures further described in Example 2. Transgenic soybean hairy root events were generated by inoculating soybean cotyledon or hypocotyl with *Agrobacterium rhizogenes* containing the SoyPyk20::GUS vector. Putative transformation events were selected and tested by GUS staining and quantitative GUS assay.

Quantitative GUS assays were performed as follows: soybean roots were homogenized in tubes containing 400 µL of extraction buffer (50 mM $K_2HPO_4$, pH 7.8; 10 mM EDTA; 1 mM DTT). Samples were centrifuged at 5000 g for 10 min. Supernatants were collected for Bradford and GUS assays, and one microgram of total protein was then used in a standard quantitative GUS activity assay using the GUS-Light™ kit (TROPIX) according to the manufacturer's protocol. Protein concentration was measured using the Protein Assay kit from Bio-Rad.

As shown in FIG. 2, 24 SoyPyk20 root events were identified as GUS positive. Four events were selected for study of GUS expression at SCN feeding sites as further described in Example 4.

Example 2

Expression of GUS Under the Control of the Soybean Pyk20 Promoter in Soybean Hairy Roots

*Agrobacterium rhizogenes* strain K599 was used for the soybean hairy root transformation. Stocks of *Agrobacterium* were maintained on minimal A media (see recipes, below). Plasmid SoyPyk20::GUS (PHP 18280) DNA was introduced into *A. rhizogenes* strain K599 using the freeze-thaw method, as described in Ha (1988) "Binary Vector" in *Plant Molecular Manual*, eds. Gelvin, Schilperoort, and Verma, pp. A3/1–A3/7.

Soybean seeds were surface-sterilized with chlorine gas at room temperature for 12–16 hours. The seeds were then aerated in a clean air hood for at least 30 minutes. Seeds were germinated and cultured in Magenta™ boxes (Magenta Corporation) containing sterile potting soil with 10 to 15 mL of 25% Gamborg's B-5 Basal medium with minimal organics (G5893, Sigma). The boxes were placed under a mix of fluorescent and incandescent lights providing a 16-hour day/8-hour night cycle and constant temperature of about 26° C. Six-day-old seedlings of non-transformed plants were inoculated with a freshly grown culture of *A. rhizogenes* previously transformed with SoyPyk20::GUS. The transformed *A. rhizogenes* was introduced into the hypocotyls just under the cotyledons by wounding 4 to 6 times in the epidermal cell layer with a 23-gauge needle containing the *A. rhizogenes*. The inoculated plants were cultured under the same conditions as those described above for seed germination.

After the soybean hypocotyls were inoculated with *A. rhizogenes*, adventitious soybean roots developed and were excised. Initially these putative transformed roots were cultured in liquid 0 B-5 medium with antibiotics to cure the roots of any bacteria; antibiotics included 500 mg/L cefotaxime (Calbiochem-Novabiochem, La Jolla, Calif.) and 200 mg/L vancomycin (Spectrum Quality Products, Los Angeles, Calif.). Roots were transferred to fresh liquid medium every 2–3 days; this transfer to fresh media was performed a total of three times. After the third transfer, each root was moved to a plate of MXB medium with Gelrite™ gelling agent. To determine whether roots had been transformed, a 1–2 cm root piece was placed in a 1.5 mL tube with GUS staining solution (0.05% X-Gluc in 100 mM sodium phosphate buffer at pH 7.0 containing 10 mM EDTA, 0.1% Triton, and 0.5 mM $K_4Fe(CN)_6.6H_2O$). Roots were incubated in this solution for 2 to 4 hours at 27 to 29° C.; solutions were then evaluated for development of the blue color indicative of GUS activity. Roots testing positive by this assay and control roots that had not been transformed were cultured in MXB medium with Gelrite™ gelling agent in an incubator without light at 260 to 30° C. A 1–4 cm piece of root tip was excised and transferred to fresh medium every 2–4 weeks.

Roots testing positive for transformation with SoyPyk20::GUS were assayed for responsiveness to infection by soybean cyst nematode ("SCN"). Roots were transferred to 6-well plates containing MXB medium with Daishiin agar. After 4–10 days, roots were inoculated with second-stage SCN juveniles (See, Lauritis et al. (1983) *J. Nematology* 15: 272–281; Savka et al. (1990) *Phytopathology* 80: 503–508; and Hermsmeier et al. (1998) *Mol. Plant-Microbe Interactions* 11(12) 1258–63). Two to five root tips were placed in each well of a 6-well culture dish; four of the wells contained roots transformed with *A. rhizogenes* containing SoyPyk20::GUS and the other two wells contained control roots transformed with *A. rhizogenes* not containing SoyPyk20::GUS. One sample of control roots used in this assay was an SCN-compatible control root sample from an SCN-susceptible or "compatible" soybean genotype such as Pioneer 93B82. The other sample of control roots was from an SCN-resistant soybean genotype ("Jack" cultivar) and was thus an SCN-resistant or "incompatible" control sample. Roots were inoculated by placing 500 second-stage SCN race 3 juveniles directly onto the roots in each well and incubating for 7 to 28 days at 260 to 28° C.

The following stock solutions and media were used for transformation and regeneration of soybean roots:

Stock Solutions (Per Liter):
  B-5 Majors: 25.00 g $KNO_3$, 1.34 g $(NH_4)_2SO_4$, 2.50 g $MgSO_4.7H_2O$, 1.50 g $CaCl_2.2H_2O$, 1.31 g $NaH_2PO_4$ (anhydrous).
  B-5 Minors: 1.00 g $MnSO_4.H_2O$, 0.30 g $H_3BO_3$, 0.20 g $ZnSO_4.7H_2O$, 0.075 g KI.
  B-5 Vitamin B-5 Stock with Thiamine: 1 L Vitamin B-5 Stock, 1 g Thiamine HCl.
  Iron Mix: 3.73 g. $Na_2EDTA$, 2.78 g $FeSO_4.7H_2O$.

Media (Per Liter):
  Minimal A medium: 10.5 g $K_2HPO_4$, 4.5 g $KH_2PO_4$, 1.0 g $(NH_4)_2SO_4$, 0.5 g $(Na)_2C_6H_5O_7.2H_2O$, 1 mL 1.0 M $MgSO_4.7H_2O$, 10 mL 20% w/v sucrose, 15 g agar.
  0 B-5 medium: 0.6 g MES (2-(N-Morpholino) ethanesulfonic acid (M5287, Sigma)), 20 g sucrose, 10 mL B-5 minors, 100 mL B-5 majors, 10 mL B-5 Vitamin Stock with Thiamine, 10 mL Iron mix.
  MXB medium: Murashige and Skoog Basal nutrient salts (M5524, Sigma), 10 mL Vitamin B-5 Stock with Thiamine, 30 g sucrose.
  MXB medium with Gelrite: add 3 g Gelrite™ gelling agent to 1 L MXB medium, pH 5.7.
  MXB medium with Daishiin agar: add 8 g Daishiin agar to 1 L MXB medium, pH 6.5.

Example 3

Expression of GUS Under the Control of the Soybean Pyk20 Promoter in Transgenic Soybean The ability of the Soybean Pyk20 promoter to direct the expression of GUS in stably transformed transgenic plants is analyzed. Somatic soybean embryo cultures are transformed, soybean plants are regenerated, and the presence of GUS activity is visualized after submerging the samples in GUS staining buffer and incubating for 16 hours at 37° C. (GUS staining buffer: 0.05% X-Gluc in 100 mM sodium phosphate buffer, pH 7.0, containing 10 mM EDTA, 0.1% Triton, and 0.5 mM $K_4Fe(CN)_6H_2O$)). The presence of active GUS is indicated by the production of blue color.

Transformation of Somatic Soybean Embryo Cultures and Regeneration of Soybean Plants.

Soybean embryogenic suspension cultures are cotransformed with SoyPyk20::GUS and a construct comprising the CaMV 35S promoter operably linked to a gene encoding hygromycin resistance (35S::hyg$^r$). Transformations are performed by the method of particle gun bombardment, and transformants carrying the SoyPyk20::GUS construct are identified.

The following stock solutions and media are used for transformation and regeneration of soybean plants:

Stock Solutions (Per Liter):
  MS Sulfate 100× Stock: 37.0 g $MgSO_4.7H_2O$, 1.69 g $MnSO_4.H_2O$, 0.86 g $ZnSO_4.7H_2O$, 0.0025 g $CuSO_4.5H_2O$.
  MS Halides 100× Stock: 44.0 g $CaCl_2.2H_2O$, 0.083 g KI, 0.00125 g $CoCl_2.6H_2O$, 17.0 g K $H_2PO_4$, 0.62 g $H_3BO_3$, 0.025 g $Na_2MoO_3.2H_2O$, 3.724 g $Na_2EDTA$, 2.784 g $FeSO_4.7H_2O$.
  2,4-D: 10 mg/mL.
  Vitamin B5 Stock: 10.0 g myo-inositol, 0.10 g nicotinic acid, 0.10 g pyridoxine HCl.

Media (Per Liter):
  SB55: 10 mL of each MS stock, 1 mL B5 Vitamin stock, 0.8 g $NH_4NO_3$, 3.033 g $KNO_3$, 1 mL 2,4-D stock, 0.667 g asparagine, pH 5.7.
  SB103: 1 pk. Murashige & Skoog salt mixture, 60 g maltose, 2 g gelrite, pH 5.7.
  SB71-1: Gamborg's B5 salts (Gibco-BRL Catalog No. 21153-028), 1 mL B5 vitamin stock, 30 g sucrose, 750 mg $MgCl_2$, 2 g Gelrite, pH 5.7.

Soybean embryonic suspension cultures are maintained in 35 mL liquid media (SB55) on a rotary shaker (150 rpm) at 28° C. with a mix of fluorescent and incandescent lights providing a 16 hour day/8 hour night cycle. Cultures are subcultured every 2 to 3 weeks by inoculating approximately 35 mg of tissue into 35 mL of fresh liquid media.

Soybean embryonic suspension cultures are transformed by the method of particle gun bombardment (see Klein et al. (1987) *Nature* 327:70–73) using a DuPont Biolistic PDS1000/He instrument.

Five μL of a 1:2 mixture of SoyPyk20::GUS construct at 0.18 μg/μL and 35S::hyg$^r$ at 0.5 μg/μL plasmid DNA are combined with 50 μL $CaCl_2$ (2.5 M) and 20 μL spermidine (0.1 M) and added to 50 μL of a 60 mg/mL 0.6 μm gold particle suspension. The mixture is agitated for 3 minutes, spun in a microfuge for 10 seconds, and the supernatant removed. The DNA-coated particles are then washed once with 400 μL of 100% ethanol and resuspended in 40 μL of anhydrous ethanol. The DNA/particle suspension is sonicated three times for 1 second each. Five μL of the DNA-coated gold particles is then loaded on each macrocarrier disk.

Approximately 300 to 400 mg of two-week-old suspension culture is placed in an empty 60 mm×15 mm petri dish and the residual liquid removed from the tissue using a pipette. The tissue is placed about 3.5 inches away from the retaining screen and bombarded twice. Membrane rupture pressure is set at 1100 psi and the chamber is evacuated to −28 inches of Hg. Two plates are bombarded, and following bombardment, the tissue is divided in half, placed back into liquid media, and cultured as described above.

Seven days after bombardment, the liquid media is exchanged with fresh SB55 containing 50 mg/mL hygromycin. The selective media is refreshed weekly. Seven weeks post-bombardment, green, transformed tissue is observed growing from untransformed, necrotic embryogenic clusters. Isolated green tissue is removed and inoculated into individual flasks to generate new, clonally-propagated, transformed embryogenic suspension cultures. Thus, each new line is treated as an independent transformation event. These suspensions can then be maintained as suspensions of embryos clustered in an immature developmental stage through subculture or can be regenerated into whole plants by maturation and germination of individual somatic embryos.

Transformed embryogenic clusters are removed from liquid culture and placed on solid agar media (SB103) containing no hormones or antibiotics. Embryos are cultured for eight weeks at 26° C. with mixed florescent and incandescent lights on a 16 hour day:8 hour night schedule. During this period, individual embryos are removed from the clusters and analyzed at various stages of embryo development. Selected lines are assayed by PCR for the presence of the chimeric gene, containing the Pyk20 promoter and the GUS gene, using Primer GUS-1 (SEQ ID NO: 9) and GUS-2 (SEQ ID NO: 10)

GUS-1: TTATGCGGGCAACGTCTGGTATC

GUS-2: GCAGCAGTTTCATCAATCACCACG

These amplifications will produce an approximately 876 bp fragment in tissues containing the chimeric gene, which is not present in tissues from wild type soybean embryos. The 876 bp fragment is indicative of the GUS coding region. Somatic embryos become suitable for germination after four weeks and are then removed from the maturation medium and dried in empty Petri dishes for 1 to 5 days. The dried embryos are then planted in SB71-1 medium where they are allowed to germinate under the same light and germination conditions described above. Germinated embryos are transferred to sterile soil and grown to maturity.

GUS Expression Analysis.

Individual T0 transgenic plants obtained from the above transformation experiment are assayed for the presence of GUS. Whole seedling plants are assayed with GUS buffer as described above and GUS expression is expected to be observed in roots, stems, leaves, and strong activity is expected in petioles, indicating that the Soybean Pyk20 promoter has activities in various soybean tissues.

Example 4

Histochemical Analysis of GUS Expression in SCN Syncytium

Root samples were infected with SCN and collected at different time points after inoculation. These samples were fixed in 0.1% glutaraldehyde in 25 mM phosphate buffer and infiltrated using a vacuum at 15 psi for 2 min. After washing in 25 mM phosphate buffer, root samples were immersed in GUS staining solution (0.05% 5-bromo-4,4-chloro-indolyl-β-D-glucuronide in 100 mM sodium phosphate buffer, pH 7.0, containing 10 mM EDTA, 0.1% Triton, and 0.5 mM $K_4Fe(CN).6H_2O$) and infiltrated for 2 min at 15 psi. The GUS staining was continued at 37° C. for 12 hours. Root samples were then boiled in acid fuschin solution for 2 minutes and destained in acidic glycerin (100 mL of glycerin and 500 μL of HCl). Samples were examined under a dissecting microscope for SCN-hairy roots interaction and GUS expression patterns. Dissected root segments for thin section were fixed in 3% glutaraldehyde in 25 mM phosphate buffer for 2 hours and washed three times in 25 mM phosphate buffer for 30 min. Root tissues were dehydrated through an ethanol series of 30%, 50%, 70%, 95%, and three changes in 100% ethanol, with a 30-minute incubation per change. A gradual buffer exchange was then carried out to replace ethanol with Histoclear (100%) and then paraffin at 60° C. Roots were thin-sectioned (10 µm) with a Leica™ microtome, and whole root samples or thin sections were examined under dissecting and light microscopy.

Histochemical analysis indicated that the SoyPyk20 promoter showed strong activity in vascular tissues. Further, the activity of the SoyPyk20 promoter was induced by SCN infection. Strong GUS activity was clearly visible in the area surrounding nematode infection. Similar results were obtained using the *Arabidopsis* Pyk20 promoter.

Example 5

Transformation and Regeneration of Transgenic Plants

Immature maize embryos from greenhouse donor plants are bombarded with a plasmid containing the soybean Pyk20 gene operably linked to a promoter such as maize Ubi-1 promoter (Christensen et al. (1992) *Plant Mol. Biol.* 13(18): 675–689) and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as described below. Media recipes follow below.

Preparation of Target Tissue

The ears are husked and surface sterilized in 30% Clorox™ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the Pyk20 gene operably linked to a synthetic promoter comprising the Pyk20 promoter sequences is made. This plasmid DNA plus plasmid DNA containing a PAT selectable marker is precipitated onto 1.1 µm (average diameter) tungsten pellets using a $CaCl_2$ precipitation procedure as follows:

100 µL prepared tungsten particles in water
10 µL (1 µg) DNA in Tris EDTA buffer (1 µg total DNA)
100 µL 2.5 M $CaCl_2$
10 µL 0.1 M spermidine Each reagent is added sequentially to the tungsten particle suspension, which is maintained on a multitube vortexer. The final mixture is sonicated briefly and allowed to incubate under constant vortexing for 10 minutes. After the precipitation period, the tubes are centrifuged briefly, liquid removed, washed with 500 mL of 100% ethanol, and centrifuged for 30 seconds. Again the liquid is removed, and 105 µL of 100% ethanol is added to the final tungsten particle pellet. For particle gun bombardment, the tungsten/DNA particles are briefly sonicated and 10 µL is spotted onto the center of each macrocarrier and allowed to dry for about 2 minutes before bombardment.

Particle Gun Treatment

The sample plates are bombarded at the manufacturer's recommended levels in a particle gun commercially available from BioRad Laboratories, Hercules, Calif. All samples receive a single shot at 650 psi, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to a 2.5" pot) containing potting soil and grown for 1 week in a growth chamber, the plants are subsequently grown an additional 1–2 weeks in the greenhouse, then transferred to classic 600 pots (1.6 gallon) and grown to maturity.

Bombardment and Culture Media

Bombardment medium (560Y) comprises 4.0 g/L N6 basal salts (SIGMA C-1416), 1.0 mL/L Eriksson's Vitamin Mix (1000× SIGMA-1511), 0.5 mg/L thiamine HCl, 120.0 g/L sucrose, 1.0 mg/L 2,4-D, and 2.88 g/L L-proline (brought to volume with d-I $H_2O$ following adjustment to pH 5.8 with KOH); 2.0 g/L Gelrite™ gelling agent (added after bringing to volume with d-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, and 2.0 mg/L 2,4-D (brought to volume with d-I $H_2O$ following adjustment to pH 5.8 with KOH); 3.0 g/L Gelrite™ (added after bringing to volume with d-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCl, 0.10 g/L pyridoxine HCl, and 0.40 g/L glycine brought to volume with polished dI $H_2O$) (Murashige and Skoog (1962) *Physiol. Plant* 15:473), 100 mg/L myo-inositol, 0.5 mg/L zeatin, 60 g/L sucrose, and 1.0 mL/L of 0.1 mM abscisic acid (brought to volume with polished dI $H_2O$ after adjusting to pH 5.6); 3.0 g/L Gelrite™ (added after bringing to volume with dI $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished dI $H_2O$), 0.1 g/L myo-inositol, and 40.0 g/L sucrose (brought to volume with polished dl $H_2O$ after adjusting pH to 5.6); and 6 g/L Bacto-Agar (added after bringing to volume with polished dI $H_2O$), sterilized and cooled to 60° C.

Example 6

*Agrobacterium*-Mediated Transformation

For *Agrobacterium*-mediated transformation of maize with a soybean Pyk20 gene operably linked to a maize Ubi-1 promoter or a synthetic promoter comprising the Pyk20 promoter sequences of the present invention, the method of Zhao may be employed (U.S. Pat. No. 5,981,840 and WO98/32326; which are hereby incorporated by reference). Briefly, immature embryos are isolated from maize and the embryos are contacted with a suspension of *Agrobacterium*, where the bacteria are capable of transferring the Pyk20 construct to at least one cell of at least one of the immature embryos (step 1: the infection step). In this step the immature embryos may be immersed in an *Agrobacterium* suspension for the initiation of inoculation. The embryos are co-cultured for a time with the *Agrobacterium* (step 2: the co-cultivation step). The immature embryos may be cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos may be cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos may be cultured on solid medium with a selective agent resulting in the selective growth of transformed cells. The callus is then regenerated into plants (step 5: the regeneration step), and calli grown on medium, e.g., selective medium, are cultured on solid medium to regenerate the plants.

Example 7

Soybean Embryo Transformation

Soybean embryos are bombarded with a plasmid containing the Pyk20 gene operably linked to a synthetic promoter (as described in U.S. Pat. No. 6,072,050) or a synthetic promoter comprising the Pyk20 promoter sequences of the present invention, as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures are maintained in 35 mL liquid media on a rotary shaker at 150 rpm and 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont® Biolistic PDS1000®/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the Pyk20 gene operably linked to a synthetic promoter can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm Petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/mL hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

All publications, patents and patent applications mentioned in the specification are indicative of the level of those skilled in the art to which this invention pertains. All publications, patents and patent applications are herein incorporated by reference to the same extent as if each individual publication, patents or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claim.

What is claimed is:

1. A nucleic acid molecule comprising a heterologous nematode-resistance sequence operably linked to a promoter that drives expression of said heterologous nematode-resistance sequence in a plant cell, wherein said promoter comprises a nucleotide sequence selected from the group consisting of:
   (a) the nucleotide sequence set forth in SEQ ID NO:3; and
   (b) the nucleotide sequence deposited as Patent Deposit No. PTA-4028.

2. A vector comprising the nucleic acid molecule of claim 1.

3. A plant cell having stably incorporated into its genome the nucleic acid molecule of claim 1.

4. The plant cell of claim 3, wherein said plant cell is from a dicot plant.

5. The plant cell of claim 4, wherein said dicot plant is soybean.

6. A method of modulating the expression of a nucleotide sequence of interest in a plant cell, said method comprising stably incorporating in the genome of a plant cell said nucleotide sequence of interest operably linked to a promoter, wherein said promoter is selected from the group consisting of:
   (a) the nucleotide sequence set forth in SEQ ID NO:3; and
   (b) the nucleotide sequence deposited as Patent Deposit No. PTA-4028.

7. A nucleic acid molecule comprising a first nucleotide sequence comprising a heterologous nematode-resistance sequence operably linked to a first promoter that induces transcription of said heterologous nematode-resistance sequence in a plant cell and a second nucleotide sequence comprising a sequence that inhibits said heterologous nematode-resistance sequence operably linked to a second promoter capable of repressing transcription of said inhibitor of said heterologous nematode-resistance sequence in a plant cell, wherein said first promoter comprises a nucleotide sequence selected from the group consisting of:
   (a) the nucleotide sequence set forth in SEQ ID NO:3; and
   (b) the nucleotide sequence deposited as Patent Deposit No. PTA-4028.

8. An expression cassette comprising the nucleic acid molecule of claim 7.

9. A plant cell having stably incorporated in its genome the nucleic acid molecule of claim 7.

10. The plant cell of claim 9, wherein said plant cell is from a dicot plant.

11. The plant cell of claim 10, wherein said dicot plant is soybean.

12. A plant stably transformed with a nucleic acid molecule comprising a heterologous nematode-resistance sequence operably linked to a promoter that induces transcription of said nematode-resistance sequence in a plant cell in response to a nematode stimulus, wherein said promoter comprises a nucleotide sequence selected from the group consisting of:
   (a) the nucleotide sequence set forth in SEQ ID NO:3; and
   (b) the nucleotide sequence deposited as Patent Deposit No. PTA-4028.

13. The plant of claim 12, wherein said plant is a dicot.

14. The plant of claim 13, wherein said dicot is soybean.

15. Transformed seed of the plant of claim 12, wherein the seed comprise the nucleic acid molecule.

16. A method for conferring or improving nematode resistance in a plant, said method comprising transforming said plant with a nucleic acid molecule comprising a heterologous sequence operably linked to a promoter that induces transcription of said heterologous sequence in a plant cell in response to a nematode stimulus and regenerating a stably transformed plant, wherein said promoter comprises a nucleotide sequence selected from the group consisting of:
   (a) the nucleotide sequence set forth in SEQ ID NO:3; and
   (b) the nucleotide sequence deposited as Patent Deposit No. PTA-4028.

17. The method of claim 16, wherein said plant is a dicot.

18. The method of claim 17, wherein said dicot is soybean.

19. A nucleic acid construct comprising a promoter, where said promoter regulates transcription of an operably linked encoding nucleotide sequence, wherein the promoter comprises a nucleotide sequence selected from the group consisting of:
   (a) the nucleotide sequence set forth in SEQ ID NO: 3; and
   (b) the nucleotide sequence deposited as patent Deposit No. PTA-4028.

20. An expression vector comprising the nucleic acid construct of claim 19.

21. A nucleic acid molecule comprising a heterologous nematode-resistance sequence operably linked to a promoter that drives expression of said heterologous nematode-resistance sequence in a plant cell, wherein said promoter comprises the nucleotide sequence set forth in SEQ ID NO:3.

* * * * *